United States Patent
Zhou et al.

(10) Patent No.: US 11,371,026 B2
(45) Date of Patent: Jun. 28, 2022

(54) DOXA PROTEIN MUTANT, AND CODING GENE AND APPLICATIONS THEREOF

(71) Applicant: Zhejiang Hisun Pharmaceutical Co., Ltd., Taizhou (CN)

(72) Inventors: Min Zhou, Zhejiang (CN); Xing Jiang, Zhejiang (CN); Shuang Han, Zhejiang (CN); Yingying He, Zhejiang (CN); Linghui Zheng, Zhejiang (CN)

(73) Assignee: Zhejiang Hisun Pharmaceutical Co., Ltd., Taizhou (CN)

( * ) Notice: Subject to any disclaimer, the term of this patent is extended or adjusted under 35 U.S.C. 154(b) by 536 days.

(21) Appl. No.: 16/301,377

(22) PCT Filed: May 8, 2017

(86) PCT No.: PCT/CN2017/083485
§ 371 (c)(1),
(2) Date: Jul. 9, 2020

(87) PCT Pub. No.: WO2017/198085
PCT Pub. Date: Nov. 23, 2017

(65) Prior Publication Data
US 2021/0032606 A1    Feb. 4, 2021

(30) Foreign Application Priority Data

May 16, 2016   (CN) .......................... 201610323073.3

(51) Int. Cl.
*C12N 15/76* (2006.01)
*C12N 9/02* (2006.01)
*C12P 19/56* (2006.01)

(52) U.S. Cl.
CPC ............ *C12N 9/0073* (2013.01); *C12N 15/76* (2013.01); *C12P 19/56* (2013.01); *C12Y 114/13* (2013.01)

(58) Field of Classification Search
CPC .......... C12N 15/52; C12N 15/76; C12P 19/56
See application file for complete search history.

(56) References Cited

U.S. PATENT DOCUMENTS

2010/0143977 A1   6/2010   Lambert et al.
2010/0255543 A1   10/2010  Sumida et al.

FOREIGN PATENT DOCUMENTS

WO   WO 96/27014 A1   9/1996

OTHER PUBLICATIONS

Extended European Search Report and Opinion dated Dec. 12, 2019 for EP Application No. 17798648.6. 8 pages.
International Preliminary Report on Patentability dated Nov. 20, 2018 for PCT/CN2017/083485. 10 pages. (In Chinese with English translation).
International Search Report and Written Opinion dated Jul. 28, 2017 for PCT/CN2017/083485. 19 pages. (In Chinese with English translation).
Lomovskaya, et al. Doxorubicin overproduction in Streptomyces peucetius: cloning and characterization of the dnrU ketoreductase and dnrV genes and the doxA cytochrome P-450 hydroxylase gene. J Bacteriol. Jan. 1999;181(1):305-18.
Lomovskaya, et al. GenBank: AAD04715.1, daunorubicin C-14 hydroxylase [Streptomyces peucetius] NCBI GenBank, Jan. 13, 1999.
Madduri, et al. Production of the antitumor drug epirubicin (4'-epidoxorubicin) and its precursor by a genetically engineered strain of Streptomyces peucetius. Nat Biotechnol. Jan. 1998;16(1):69-74.

*Primary Examiner* — Karen Cochrane Carlson
(74) *Attorney, Agent, or Firm* — Sheppard Mullin Richter & Hampton LLP

(57) ABSTRACT

The present invention relates to a DoxA protein mutant having an amino acid sequence set forth in SEQ ID NO: 16, and coding gene thereof. The protein mutant or the coding gene thereof can be used for producing epirubicin. The present invention further relates to a *Streptomyces* capable of efficiently expressing epirubicin, which is constructed by replacing the dnmV gene of a starting *Streptomyces* in situ with the avrE gene and mutating the doxA gene of the starting *Streptomyces* into a gene encoding the protein set forth in SEQ ID NO: 16. The fermentation broth of this *Streptomyces* has an epirubicin potency of up to 102.0 µg/ml.

13 Claims, 3 Drawing Sheets

Specification includes a Sequence Listing.

DOXA PROTEIN MUTANT, AND CODING GENE AND APPLICATIONS THEREOF

CROSS REFERENCE TO RELATED APPLICATIONS

The present application is a national stage application of International Application PCT/CN2017/083485, filed May 8, 2017, which claims priority to Chinese Patent Application No. 201610323073.3, filed May 16, 2016, the contents of which are incorporated by reference in their entireties into the present disclosure.

FIELD OF THE INVENTION

The invention relates to the technical fields of bioengineering and pharmacy, specifically to a DoxA protein mutant, and coding gene and applications thereof.

SEQUENCE LISTING

The instant application contains a Sequence Listing which has been submitted in ASCII format via EFS-Web and is hereby incorporated by reference in its entirety. Said ASCII copy, created on Nov. 13, 2018, is named 60SG-279103 SEQ_SL.txt and is 25,636 bytes in size.

BACKGROUND OF THE INVENTION

Anthracycline anti-tumor drugs can be widely used to treat malignant tumor diseases such as leukemia, breast cancer, stomach cancer and intestinal cancer, and are clinically large-scale drugs. Among them, epirubicin has a wider clinical application because of its high activity and low toxicity.

Epirubicin is currently produced by semi-synthetic methods. However, the chemical synthesis process is complicated, the cost is high, and the reaction conditions are strict; at the same time, a large amount of chemical solvent is used in the production process, which is likely to cause environmental pollution. Therefore, the pursuit of microbial fermentation which is a green production process to produce epirubicin has received widespread attention. Researchers at the University of Wisconsin in the United States reported in 1998 the use of combinatorial biology methods to replace the keto-reductase gene dnmV of the adriamycin-producing strain ATCC29050 with avrE, and successfully constructed genetically engineered strain producing the epidaunorubicin and epirubicin (FIG. 1), but only trace amount of epirubicin is produced, the metabolites are mainly its precursor, epidaunorubicin. US20100255543A1 replaced dnmV with evaE, and the epidaunorubicin potency was nearly doubled compared to the strain replaced with avrE, reaching 173 μg/ml, but no epirubicin was produced. In 2006, Zhu Baoquan of Shanghai Pharmaceutical Industry Research Institute carried out corresponding genetic engineering on *Streptomyces coeruleorubidus*, and a small amount of epidaunorubicin could be obtained by fermentation. US20100143977A1 disclosed a genetic engineering modification method for obtaining 700 μg/ml epidaunorubicin by fermentation of *Streptomyces*.

In summary, it is currently possible to obtain an epidaunorubicin high-producing strain by genetic modification of the strain, but only a small amount of epirubicin is produced. Epirubicin is produced following the catalysis of epidaunorubicin by DoxA, so screening for highly active doxA mutants is the key to solve this problem.

SUMMARY OF THE INVENTION

The technical problem to be solved by the present invention is to prepare epirubicin and increase the yield of epirubicin.

In order to solve the above technical problem, the present invention provides a protein having an amino acid sequence set forth in SEQ ID NO: 16.

The protein is a DoxA protein mutant, which can be artificially synthesized, or can be obtained by firstly synthesizing its encoding gene and then conducting protein expression in organisms.

In order to solve the above technical problem, the present invention further provides a biological material related to the protein, which is the following B1) or B2):

B1) nucleic acid molecule encoding the protein;
B2) expression cassette, recombinant vector, recombinant microorganism or transgenic cell line comprising the nucleic acid molecule of B1).

Wherein, the nucleic acid molecule of B1) can be DNA, such as cDNA, genomic DNA or recombinant DNA; the nucleic acid molecule can also be RNA, such as mRNA or hnRNA;

The expression cassette comprising the nucleic acid molecule encoding the protein in B2) refers to a DNA molecule capable of expressing the protein in a host cell, and the DNA molecule can include not only a promoter that initiates transcription of a gene encoding the protein, but also can include a terminator that terminates transcription of a gene encoding the protein; further, the expression cassette may further comprise an enhancer sequence;

The recombinant microorganism may specifically be bacteria, algae and fungi, wherein the bacteria may be *Streptomyces*.

In the above biological material, the nucleic acid molecule of B1) is a gene represented by the following 1) or 2) or 3):

1) a DNA molecule having a nucleotide sequence set forth in SEQ ID NO: 15;
2) a DNA molecule that hybridizes to the DNA molecule as defined in 1) under stringent conditions and encodes the protein;
3) a DNA molecule having 90% or more identity to the DNA molecule as defined in 1) or 2) and encoding the protein.

In the above biological material, the stringent conditions may be as follows: hybridization in a mixed solution of 7% sodium dodecyl sulfate (SDS), 0.5 M $Na_3PO_4$ and 1 mM EDTA at 50° C. with washing in 2×SSC, 0.1% SDS at 50° C.; also: hybridization in a mixed solution of 7% SDS, 0.5 M $Na_3PO_4$ and 1 mM EDTA at 50° C. with washing in 1×SSC, 0.1% SDS at 50° C.; also: hybridization in a mixed solution of 7% SDS, 0.5 M $Na_3PO_4$ and 1 mM EDTA at 50° C. with washing in 0.5×SSC, 0.1% SDS at 50*C; also: hybridization in a mixed solution of 7% SDS, 0.5 M $Na_3PO_4$ and 1 mM EDTA at 50° C. with washing in 0.1×SSC, 0.1% SDS at 50° C.; also: hybridization in a mixed solution of 7% SDS, 0.5 M $Na_3PO_4$ and 1 mM EDTA at 50° C. with washing in 0.1×SSC, 0.1% SDS at 65° C.; also: hybridization in a mixed solution of 6×SSC and 0.5% SDS at 65° C. with washing the membrane once in 2×SSC, 0.1% SDS and once in 1×SDS, 0.1% SDS at 65° C.

The identity of 90% or more can be 91%, 92%, 93%, 94% or 95% or more.

One of ordinary skill in the art can readily mutate the nucleotide sequence encoding the protein of the present invention using known methods, such as directed evolution and point mutation. Those artificially modified nucleotides having a certain identity with the nucleotide sequence encoding the protein of the present invention, as long as they encode the present protein and the encoded protein has the function of the present protein, are all derived from the nucleotide sequence of the present invention and identical to the sequence of the invention.

The term "identity" as used herein refers to sequence similarity to a nucleotide sequence. "Identity" can be evaluated with the naked eye or computer software. Using computer software, the identity between two or more sequences can be expressed in percentage (%), which can be used to evaluate the identity between related sequences.

In order to solve the above technical problem, the present invention further provides a method for constructing epirubicin-expressing *Streptomyces*, comprising the steps of: replacing the dnmV gene of a starting *Streptomyces* in situ with the avrE gene, and mutating the doxA gene of the starting *Streptomyces* into a gene encoding the protein having the amino acid sequence set forth in SEQ ID NO: 16.

In the above method, the preservation number of the starting *Streptomyces* is CGMCC No. 4827.

In any one of the above methods, the sequence of the dnmV gene is set forth in SEQ ID NO: 9;

The sequence of the avrE gene is set forth in SEQ ID NO: 10;

The sequence of the gene encoding the protein set forth in SEQ ID NO: 16 is set forth in SEQ ID NO: 15.

In any one of the above methods, the method for replacing the dnmV gene of a starting *Streptomyces* in situ with the avrE gene is as follows:

(1) Constructing a vector pZH11 for the dnmV gene knockout and a vector pZH12 for replacing the dnmV gene in situ with avrE gene respectively;

(2) Transforming the pZH11 and the pZH12 into *Escherichia coli*, respectively, to obtain recombinant *Escherichia coli* containing pZH11 and recombinant *Escherichia coli* containing pZH12;

(3) Carrying out conjugal transfer of the recombinant *Escherichia coli* containing pZH11 to *Streptomyces* (CGMCC No. 4827) to obtain dnmV gene knockout strain ZH11; and (4) Carrying out conjugal transfer of the recombinant *Escherichia coli* containing pZH12 to ZH11 to obtain the epirubicin-producing strain ZH12 in which the dnmV gene was replaced in situ with the avrE gene.

In any one of the above methods, the sequence of the gene encoding the protein set forth in SEQ ID NO: 16 is set forth in SEQ ID NO: 15.

In any one of the above methods, the method of mutating the doxA gene into a gene encoding the protein having the amino acid sequence set forth in SEQ ID NO: 16 is as follows: The sequence between the restriction enzyme cutting sites SacI and BglII of pZH5 is replaced with a DNA molecule comprising the nucleotide sequence set forth in SEQ ID NO: 15 to obtain a recombinant plasmid pZH99; The sequence between the restriction enzyme cutting sites XbaI and BamHI of pSET152 is replaced with a fragment containing ermE*+the DNA molecule having the nucleotide sequence set forth in SEQ ID NO: 15 between the restriction enzyme cutting sites XbaI and BglII of the pZH99 to obtain pZH100; Transforming the pZH100 into *Escherichia coli* to obtain a recombinant *Escherichia coli* containing pZH100; Carrying out conjugal transfer of the recombinant *Escherichia coli* containing pZH100 to ZH12 to obtain the epirubicin-producing *Streptomyces*;

The sequence of the pZH5 is set forth in SEQ ID NO: 2;

The sequence of the ermE* gene is set forth in positions 46 to 325 of SEQ ID NO: 2;

The pSET152 is disclosed in the literature "Bierman M, Logan R, O'Brien K, Seno E T, Rao R N, Schoner B E. Plasmid cloning vectors for the conjugal transfer of DNA from *Escherichia coli* to *Streptomyces* spp. Gene. 1992, 116(1): 43-9", and can be obtained by the public from Zhejiang Hisun Pharmaceutical Co., Ltd.

In any one of the above methods, the method for constructing the pZH11 in step (1) is as follows: replacing the sequence between the restriction enzyme cutting sites HindIII and XbaI of pHY642 with the upstream DNA fragment of the dnmV gene to obtain pZH9; replacing the sequence between the restriction enzyme cutting sites EcoRI and XbaI of pZH9 with the downstream DNA fragment of the dnmV gene to obtain pZH10; inserting the apramycin-resistant gene fragment of pIJ773 into the restriction enzyme cutting site XbaI of pZH10 to obtain pZH11;

The method for constructing the upstream DNA fragment of the dnmV gene and the downstream DNA fragment of the dnmV gene is specifically as follows: with the genomic DNA of *Streptomyces* (CGMCC No. 4827) as a template, Dnm VLF/Dnm VLR primer pair and Dnm VRF/Dnm VRR primer pair were used respectively to amplify and obtain the upstream DNA fragment of the dnmV gene and the downstream DNA fragment of the dnmV gene;

The sequence of the Dnm VLF is set forth in SEQ ID NO: 3;

The sequence of the Dnm VLR is set forth in SEQ ID NO: 4;

The sequence of the Dnm VRF is set forth in SEQ ID NO: 5;

The sequence of the Dnm VRR is set forth in SEQ ID NO: 6;

The sequence of the pHY642 is set forth in SEQ ID NO: 1;

The pIJ773 is disclosed in the literature "Gust B I, Challis G L, Fowler K, Kieser T, Chater K F. PCR-targeted *Streptomyces* gene replacement identifies a protein domain needed for biosynthesis of the sesquiterpene soil odor geosmin. Proc Natl Acad Sci USA. 2003 Feb. 18; 100 (4): 1541-6. Epub 2003 Jan. 31", and can be obtained by the public from Zhejiang Hisun Pharmaceutical Co., Ltd.

In any one of the above methods, the method for constructing the pZH12 in step (1) is as follows: inserting avrE gene fragment into the XbaI site of the pZH10 to obtain pZH12; The method for constructing the avrE gene fragment is specifically as follows: with the genomic DNA of *Streptomyces avermitilis* as a template, avrEF/avrER is used as a primer pair to amplify and obtain the avrE gene fragment;

The sequence of the avrEF is set forth in SEQ ID NO: 7;

The sequence of the avrER is set forth in SEQ ID NO: 8;

The *Streptomyces avermitilis* is disclosed in the literature "Ikeda H, Ishikawa J, Hanamoto A, Shinose M, Kikuchi H, Shiba T, Sakaki Y, Hattori M, Omura S. Complete genome sequence and comparative analysis of the industrial microorganism *Streptomyces avermitilis*. Nat Biotechnol. 2003 May; 21(5): 526-31", and can be obtained by the public from Zhejiang Hisun Pharmaceutical Co., Ltd.

In any one of the above methods, the *Escherichia coli* is *Escherichia coli* ET12567 (pUZ8002);

The recombinant *Escherichia coli* containing pZH11 is recombinant *Escherichia coli* ET12567 (pUZ8002, pZH11);

The recombinant *Escherichia coli* containing pZH12 is recombinant *Escherichia coli* ET12567 (pUZ8002, pZH12).

In any one of the above methods, the recombinant *Escherichia coli* containing pZH100 is recombinant *Escherichia coli* ET12567 (pUZ8002, pZH100).

In order to solve the above technical problem, the present invention further provides a *Streptomyces* constructed according to any one of the above methods;

The *Streptomyces* is a doxA mutant strain, and the DoxA protein expressed by the strain has mutations of A133T, A339D and C398S compared with the *Streptomyces* (CGMCC No. 4827);

The sequence of doxA gene of *Streptomyces* (CGMCC No. 4827) is set forth in SEQ ID NO: 17, and the amino acid sequence of the DoxA protein encoded by it is set forth in SEQ ID NO: 18.

In order to solve the above technical problem, the present invention further provides a method for preparing epirubicin, which comprises subjecting the *Streptomyces* to fermentation.

In the above method, the formula (g/L) of the culture medium of the fermentation is as follows: corn starch 80.0, yeast powder 30.0, $CaCO_3$ 3.0, NaCl 3.0, the balance being water, pH 6.80.

In order to solve the above technical problem, the present invention further provides use of at least one of the following (1) to (3) in the preparation of epirubicin:
(1) The above protein;
(2) The biological material according to any one of the above;
(3) The *Streptomyces* and/or its bacterial suspension and/or its fermentation broth and/or its metabolites.

In order to solve the above technical problem, the present invention further provides use of at least one of the following (1) to (3) in preparing an anti-cancer drug:
(1) The above protein;
(2) The biological material according to any one of the above;
(3) The *Streptomyces* and/or its bacterial suspension and/or its fermentation broth and/or its metabolites.

In the above application, the anti-cancer drug is a drug against leukemia, breast cancer, gastric cancer and/or intestinal cancer.

In the present invention, after the dnmV gene of *Streptomyces* (CGMCC No. 4827) is replaced in situ with the avrE gene, the doxA gene is further subject to directed evolution by error-prone PCR, to screen and obtain a doxA mutant strain which has higher catalytic activity of catalyzing the epidaunorubicin into epirubicin. Under the conditions of the fermentation of the present invention, the epirubicin potency of the fermentation broth reaches 102.0 µg/ml and the yield of epirubicin is increased. The present invention has a good application prospect in the technical fields of bioengineering and pharmacy.

DETAILED DESCRIPTION OF THE EMBODIMENTS

Figure 1:
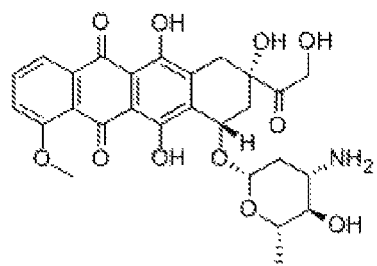
FIG. 1 shows the chemical structure of epirubicin.

The experimental methods used in the following examples are conventional methods unless otherwise specified.

The materials, reagents and the like used in the following examples are commercially available unless otherwise specified.

The present invention will now be described in detail in combination with the following examples. It is to be understood that the following examples are merely illustrative of the invention and are not intended to limit the scope of the invention.

*Streptomyces* (CGMCC No. 4827) was purchased from the China General Microbiological Culture Collection Center.

Sucrose-Tris buffer: The solute is sucrose, the solvent is 10 mM Tris-HCl, the mass percentage of sucrose in sucrose-Tris buffer is 10.3%, and the pH of the buffer is 8.0.

The lysozyme solution is a product of Sangon Biotech (Shanghai) Co., Ltd. and its catalog number is A610308.

The saturated phenol solution (pH 8.0) is a product of Sangon Biotech (Shanghai) Co., Ltd. and its catalog number is A504193.

The TSB medium (Bacto™ Tryptic Soy Broth) is a product of BD and its catalog number is 211825.

The pIJ773 is disclosed in the literature "Gust B I, Challis G L, Fowler K, Kieser T, Chater K F. PCR-targeted *Streptomyces* gene replacement identifies a protein domain needed for biosynthesis of the sesquiterpene soil odor geosmin. Proc Natl Acad Sci USA. 2003 Feb. 18; 100 (4): 1541-6. Epub 2003 Jan. 31", and can be obtained by the public from Zhejiang Hisun Pharmaceutical Co., Ltd.

The *Streptomyces avermitilis* is disclosed in the literature "Ikeda H, Ishikawa J, Hanamoto A, Shinose M, Kikuchi H, Shiba T, Sakaki Y, Hattori M, Omura S. Complete genome sequence and comparative analysis of the industrial microorganism *Streptomyces avermitilis*. Nat Biotechnol. 2003 May; 21(5): 526-31", and can be obtained by the public from Zhejiang Hisun Pharmaceutical Co., Ltd.

The *Escherichia coli* ET12567 (pUZ8002) is disclosed in the literature "Bierman M, Logan R, Obrien K, Seno E T, Rao R N, Schoner B E: Plasmid cloning vectors for the conjugal transfer of DNA from *Escherichia coli* to *Streptomyces* spp. Gene. 1992, 116(1): 43-49.10.1016/0378-1119 (92) 90627-2", and can be obtained by the public from Zhejiang Hisun Pharmaceutical Co., Ltd.

The epirubicin standard is a product of Langchem Co. and its catalog number is 10309.

The pSET152 is disclosed in the literature "Bierman M, Logan R, O'Brien K, Seno E T, Rao R N, Schoner B E. Plasmid cloning vectors for the conjugal transfer of DNA from *Escherichia coli* to *Streptomyces* spp. Gene. 1992, 116(1): 43-9", and can be obtained by the public from Zhejiang Hisun Pharmaceutical Co., Ltd.

EXAMPLES

Example 1—Construction of Plasmid pZH11 for the dnmV Gene Knockout

1. Extraction of Genomic DNA of *Streptomyces* (CGMCC No. 4827)

50 µl cell suspension of *Streptomyces* (CGMCC No. 4827) was inoculated into 30 ml of TSB medium, cultured at 28° C., 220 rpm for 48 hr, centrifuged in a 50 ml centrifuge tube at 4000 rpm for 10 min, and the supernatant was removed. The obtained precipitate was washed with 30 ml sucrose-Tris buffer twice and then suspended in 5 ml sucrose-Tris buffer. 20 µl lysozyme solution (100 mg/ml) was added and the resulting mixture was kept in 37° C. water bath for 2 hr. 500 µl of 10% SDS solution was added and the mixture was gently inverted until essentially clear. 5 ml of a saturated phenol solution (pH 8.0) was added, and after gently inverting several times, the mixture was centrifuged at 4000 rpm for 10 min. 4 ml of the upper layer solution was taken, and 4 ml of a phenol-chloroform-isoamyl alcohol (pH 8.0) solution was added, and the mixture was gently inverted several times, and then centrifuged at 4000 rpm for 10 minutes. 3 ml of the upper layer was taken, 300 µl of 3 M HAc/NaAc buffer (pH 5.3) and 3 ml of isopropanol were added, and after gently inverting several times, the pellet of the agglomeration was picked up to a 1.5 ml centrifuge tube with a pipette tip. The precipitate was washed twice with aqueous ethanol (70% by volume) and dried at room temperature. The mixture was dissolved by adding 500 µl of Tris-HCl (pH 8.0) to obtain genomic DNA of *Streptomyces* (CGMCC No. 4827).

2. Using the genomic DNA of *Streptomyces* (CGMCC No. 4827) obtained in step 1 as a template, the Dnm VLF/Dnm VLR primer pair and the Dnm VRF/Dnm VRR primer pair were used respectively to amplify and obtain the upstream DNA fragment of the dnmV gene and the downstream DNA fragment of the dnmV gene.

The sequences of the primers were as follows:

```
Dnm VLF:
                                         (SEQ ID No. 3)
5'-CCCAAGCTTCCACTCTGCCCGTCCACCTCTT-3',
(The underlined sequence is the recognition site
of restriction endonuclease HindIII)

Dnm VLR:
                                         (SEQ ID No. 4)
5'-TGCTCTAGACTCACCCGTCTCCGCGTG-3',
(The underlined sequence is the recognition site
of restriction endonuclease XbaI)

Dnm VRF:
                                         (SEQ ID No. 5)
5'-TGCTCTAGACGGGCTGGTCGTCAACATCG-3',
(The underlined sequence is the recognition site
of the restriction endonuclease XbaI)

Dnm VRR:
                                         (SEQ ID No. 6)
5'-CCGGAATTCGCTCCTTCCTGGGCTTCCTG-3'.
(The underlined sequence is the recognition site
of the restriction endonuclease EcoRI)
```

(The underlined sequence is the recognition site of the restriction endonuclease EcoRI)

According to instruction of the PrimeSTAR kit (TaKaRa, catalog number: R044A), the PCR amplification system was prepared according to the following ratio:

| | |
|---|---|
| 2 × PrimeSTAR GC buffer | 40 µl |
| 2.5 mM dNTP | 6.4 µl |
| Dnm VLF(Dnm VRF) | 0.8 µl |
| Dnm VLR(Dnm VRR) | 0.8 µl |
| template | 0.8 µl |
| H$_2$O | 30.5 µl |
| PrimeSTAR polymerase | 0.8 µl |

According to the different prime pairs, the PCR was carried out in two different tubes. The PCR procedure was: 95° C. for 5 min; 30 cycles of 95° C. for 30 sec, 55° C. for 30 sec and 72° C. for 3 min; 72° C. for 5 min; 16° C. for 1 min.

Figure 2:
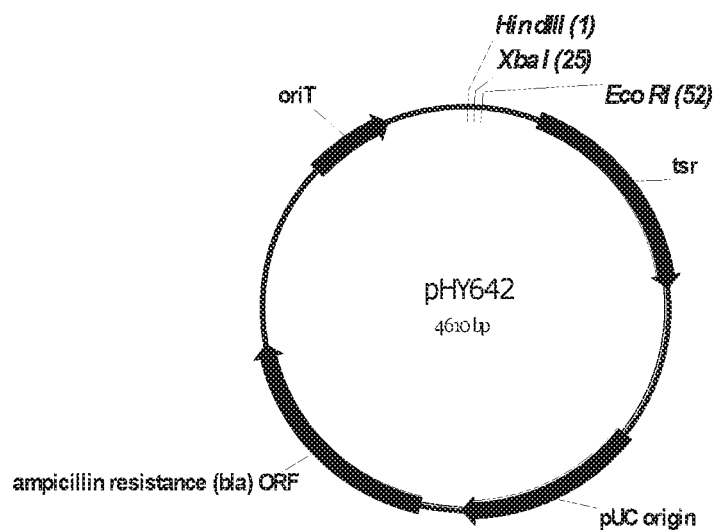
FIG. 2 is a plasmid map of pHY642, the sequence of which is set forth in SEQ ID NO: 1.

3. The upstream DNA fragment of dnmV gene obtained by PCR amplification was digested with HindIII and XbaI to obtain upstream fragment 1; vector pHY642 (FIG. 2) was digested with HindIII and XbaI to obtain vector fragment 1; the upstream fragment 1 was ligated with the vector fragment 1 to obtain a recombinant plasmid, which was named pZH9. The pZH9 was sent for sequencing and the results were in line with expectations.

The downstream DNA fragment of dnmV gene obtained by PCR amplification was digested with EcoRI and XbaI to obtain the downstream fragment 2; pZH9 was digested with EcoRI and XbaI to obtain vector fragment 2; the downstream fragment 2 was ligated with vector fragment 2 to obtain a recombinant plasmid, which was named pZH10. The pZH10 was sent for sequencing and the results were in line with expectations.

The pIJ773 was digested with XbaI to obtain an apramycin-resistant gene fragment; pZH10 was digested with XbaI to obtain vector fragment 3; and the apramycin-resistant gene fragment was ligated with the vector fragment 3 to obtain a recombinant plasmid, which was named pZH11. The pZH11 was sent for sequencing and the results were in line with the expected sequence.

pZH11 is the finally constructed vector for the dnmV gene knockout.

Example 2—Construction of Plasmid pZH12 for In Situ Replacement of dnmV Gene with avrE Gene 1. Using the genomic DNA of *Streptomyces avermitilis* as a template, avrEF/avrER primer pair was used to amplify and obtain the avrE gene fragment.

The PCR amplification system and procedure were the same as in Example 1 except that the template and the primers were different.

The sequences of the primers were as follows:
avrEF:

```
avrEF:
                                         (SEQ ID No. 7)
5'-ACGCGGAGACGGGTGAGGCGGACATGGGGCGGTTTTCGGTGTGC-
3';

avrER:
                                         (SEQ ID No. 8)
5'-GTCGTCGGAAGCCTGTGAGCTACACGTAAGCCGCCACCATG-3'.
```

2. The avrE gene fragment obtained in step 1 was digested with XbaI to obtain avrE fragment 3; pZH10 was digested with XbaI to obtain vector fragment 3; the avrE fragment 3 was ligated with the vector fragment 3 to obtain a recombinant plasmid, which was named pZH12. The pZH12 was sent for sequencing and the results were in line with the expected sequence.

pZH12 was used to replace the dnmV gene in situ with the avrE gene.

Example 3—Construction of Epirubicin-Producing Bacteria

1. Construction of recombinant *E. coli* ET12567 (pUZ8002, pZH11) and ET12567 (pUZ8002, pZH12)

pZH11 and pZH12 were transformed into *E. coli* ET12567 (pUZ8002), respectively, as follows:

1 μl of the plasmid pZH11 prepared in Example 1 and 1 μl of the plasmid pZH12 prepared in Example 2 were separately added to 100 μl of *E. coli* ET12567 (pUZ8002) competent cells, placed on ice for 30 min, and then heat-shocked at 42° C. for 90 sec, and then quickly placed on ice cooling for 1 min. 900 μl of liquid LB medium was added, and kept in 37° C. water bath for 50 min. 100 μl of each was plated on solid LB medium containing 25 μg/ml chloramphenicol (Cm), 50 μg/ml kanamycin (Km), and 50 μg/ml ampicillin (Amp), and cultured overnight at 37° C. The transformants were grown, i.e. recombinant *E. coli* ET12567 (pUZ8002, pZH11) and ET12567 (pUZ8002, pZH12).

2. Cultivation of recombinant *Escherichia coli* ET12567 (pUZ8002, pZH11) and ET12567 (pUZ8002, pZH12)

The single colonies of recombinant *Escherichia coli* ET12567 (pUZ8002, pZH11) and ET12567 (pUZ8002, pZH12) were inoculated into 3 ml of liquid LB medium containing 25 μg/ml Cm, 50 μg/ml Km and 50 μg/ml Amp. After cultured overnight at 37° C., 250 rpm, 300 μl of each was inoculated into 30 ml of liquid LB medium containing 25 μg/ml Cm, 50 μg/ml Km and 50 μg/ml Amp, and cultured at 37° C., 250 rpm for 4-6 h to an OD600 of 0.4-0.6. After centrifugation, the cells were respectively collected, washed twice with liquid LB medium, and finally, 500 μl of liquid LB medium was added to suspend the cells for use.

3. Conjugal transfer and screening of dnmV gene knockout strain ZH11

(1) Conjugal Transfer

50 μl of *Streptomyces* (CGMCC No. 4827) cell suspension was inoculated into 30 ml of TSB medium, and cultured at 28° C., 220 rpm for 48 hr. Then, 500 μl of the culture was added to 500 μl of ET12567 (pUZ8002, pZH11) cultured in step 2. 800 μl of the supernatant was removed by centrifugation. The cells were suspended in the remaining supernatant and plated on MS solid medium plates, and cultured at 28° C. for 16-20 h. Then the surface of the medium was covered with 1 ml of sterilized water containing 500 μg of apramycin (Am) and 500 μg of nalidixic acid (NaI), cultured at 28° C. for 4-8 days, and the conjugant was grown.

(2) Screening

One conjugant obtained in step (1) was inoculated by streaking on MS solid medium (20.0 g of agar, 20.0 g of mannitol, 20.0 g of soybean cake powder, and tap water was added until the final volume was 1000 ml) containing 25 μg/ml of NaI and cultured at 28° C. for 4-6 d. Each of the grown single colonies was simultaneously transferred to the following two solid media: MS solid medium containing 25 μg/ml thiostrepton (Tsr) and 25 μg/ml apramycin (Am), respectively. After cultivation at 28° C. for 5 days, the growth was observed. The colony which was grown on the MS solid medium containing apramycin (Am) while not grown on the MS solid medium containing thiostrepton was the dnmV gene knockout strain, which was named ZH11.

4. Construction of Epirubicin-Producing Strain (1) Conjugal Transfer

50 μl cell suspension of ZH11 obtained in step 3 was inoculated into 30 ml TSB medium, and cultured at 28° C., 220 rpm for 48 hr. Then, 500 μl of the culture was added to 500 μl of ET12567 (pUZ8002, pZH12) cultured in step 2. 800 μl of the supernatant was removed by centrifugation. The cells were suspended in the remaining supernatant and plated on MS solid medium plates, and cultured at 28° C. for 16-20 h. The surface of the medium was covered with 1 ml of sterilized water containing 500 μg of Tsr and 500 μg of NaI, cultured at 28° C. for 4-8 days, and the conjugant was grown.

(2) Screening

One conjugant obtained in step (1) was inoculated by streaking on MS solid medium containing 25 μg/ml of NaI and cultured at 28° C. for 4-6 d. Each of the grown single colonies was simultaneously transferred to the following two MS solid media: one contained 25 μg/ml Am, and the other contained neither Am nor Tsr. After cultivation at 28° C. for 5 days, the growth was observed. The colony, which was grown on the MS solid medium containing no Am and Tsr while not grown on the MS solid medium containing Am (i.e., indicating that dnmV was replaced with avrE), was an epirubicin-producing bacterium, which was named ZH12.

The sequence of the dnmV gene is set forth in SEQ ID NO: 9.

The sequence of the avrE gene is set forth in SEQ ID NO: 10.

Example 4—Fermentation Test of Epirubicin

1. Fermentation of Epirubicin

A loop of mycelia of ZH12 prepared in Example 3 was inoculated on the solid slant medium, and after cultivation at 28° C. for 10 days, a mass of about 1×1 cm was dug from the slant, inoculated into the seed culture medium and incubated at 28° C., 250 rpm for 45 hr to obtain seed culture. Then, 2.5 ml of the seed culture was inoculated into the fermentation medium, and cultured at 28° C., 250 rpm for 7 days to obtain a fermentation broth.

The formulations of each of the above media are as follows:

Solid slant medium (g/L): yeast extract 4.0, malt extract 10.0, glucose 4.0, agar 20.0, the balance was water, the pH was adjusted to 6.80, and the mixture was sterilized, slanted and cooled.

Seed culture medium (g/L): soluble starch 30.0, glucose 10.0, soybean cake powder 20.0, $CaCO_3$ 2.0, NaCl 3.0, the balance was water, and the pH was adjusted to 6.8.

Fermentation medium (g/L): corn starch 80.0, yeast powder 30.0, $CaCO_3$ 3.0, NaCl 3.0, the balance was water, and the pH was adjusted to 6.80.

The sterilization methods of the above media were all as follows: sterilized at 121° C. for minutes.

2. HPLC Detection

After the fermentation, the fermentation broth was adjusted to pH 1.5 with HCl, and ethanol with 3 times the volume of the mixture was added. After standing for 1 hr, the resulting mixture was centrifuged at 4000 rpm. The supernatant sample was taken for HPLC detection, and the epirubicin standard was used as a control. The epirubicin potency of the fermentation broth was calculated by multiplying the target peak area ratio of the sample and the standard by the concentration of the standard.

The HPLC detection method is as follows:

Column: C18 column, 5 μm, 4.6×250 mm;

Buffer: prepared by dissolving 1.44 g of sodium dodecyl sulfate and 0.68 ml of phosphoric acid in 500 ml of ultrapure water;

Mobile phase: buffer:acetonitrile:methanol is 500:500:60 (volume ratio);

Flow rate: 1.35 ml/min;

Detection wavelength: 254 nm;

Injection volume: 10 μl.

Figure 4:
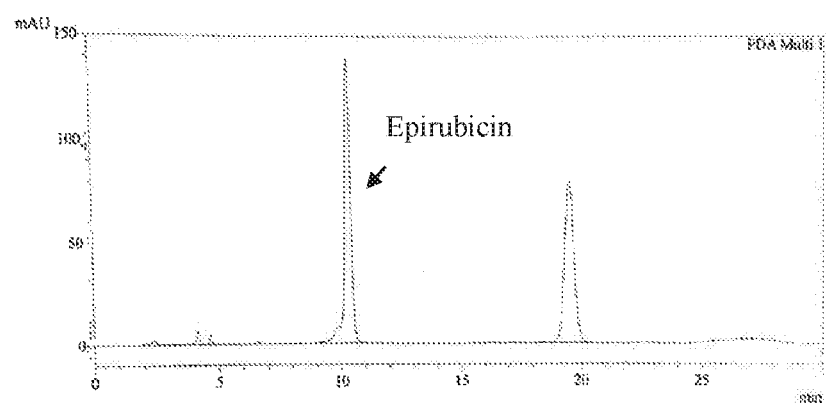
FIG. 4 is an HPLC detection profile of epirubicin standard.

The HPLC detection profile of the epirubicin standard is shown in FIG. 4, wherein the retention time of epirubicin is 10.316 min.

Figure 5:
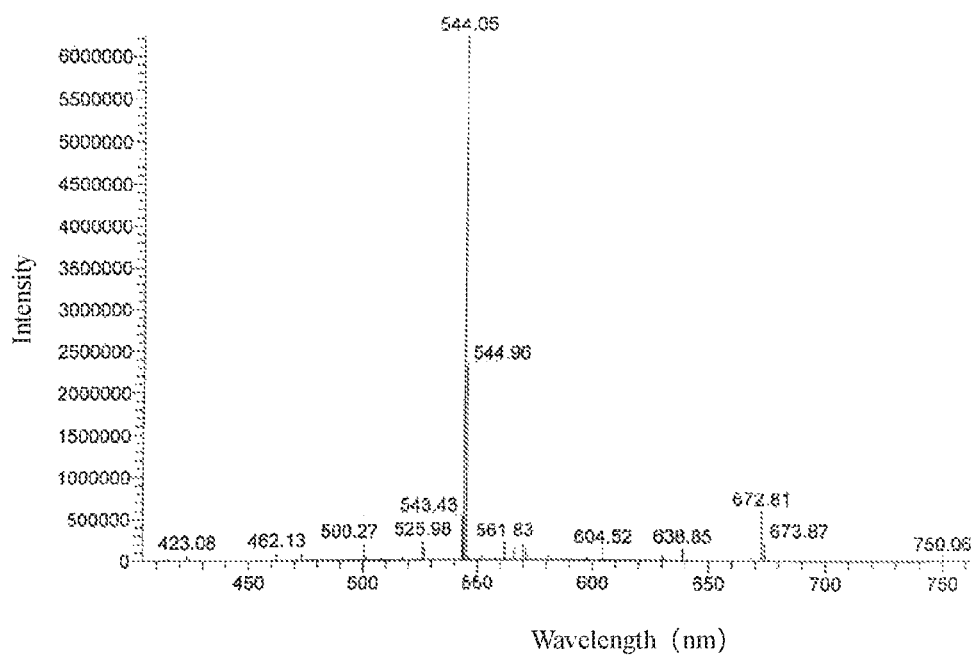
FIG. 5 is a mass spectrum of epirubicin standard.

The mass spectrum of the epirubicin standard is shown in FIG. 5.

The results showed that the epirubicin potency of the ZH12 fermentation broth was 0.65 μg/ml.

Example 5—Mutation and Cloning of the doxA Gene

1. The genomic DNA of *Streptomyces* (CGMCC No. 4827) was used as a template, DoxAF/DoxAR was used as a primer pair, and $MnCl_2$ with a final concentration of 0.5 μM was added for error-prone PCR to amplify a doxA mutant gene fragment, thereby conducting random mutation of the doxA gene.

The sequences of the primers were as follows:

DoxAF: 5'-ACA GAGCTCGTGGCCGTCGACCCGTTC-3' (SEQ ID NO: 11) (The underlined sequence is the recognition site of the restriction endonuclease SacI);

DoxAR: 5'-GGA AGATCTTCAGCGCAGCCAGACGGG-3' (SEQ ID NO: 12) (The underlined sequence is the recognition site of the restriction endonuclease BglII).

According to the instruction of Taq Polymerase kit (Sangon Biotech (Shanghai) Co., Ltd., catalog number: B500010), the PCR amplification system was prepared according to the following ratio:

| | |
|---|---|
| 10 × Taq buffer | 10 μl |
| 2.5 mM dNTP | 10 μl |
| DoxAF | 2 μl |
| DoxAR | 2 μl |
| template | 1 μl |
| 50 μm $MnCl_2$ | 1 μl |
| $H_2O$ | 73 μl |
| Taq polymerase | 1 μl |

The PCR was carried out in 4 tubes, and the PCR procedure was: 94° C. for 5 min; 30 cycles of 94° C. for 30 sec, 55° C. for 30 sec and 72° C. for 2 min; 72° C. for 5 min; 16° C. for 1 min.

Figure 3:
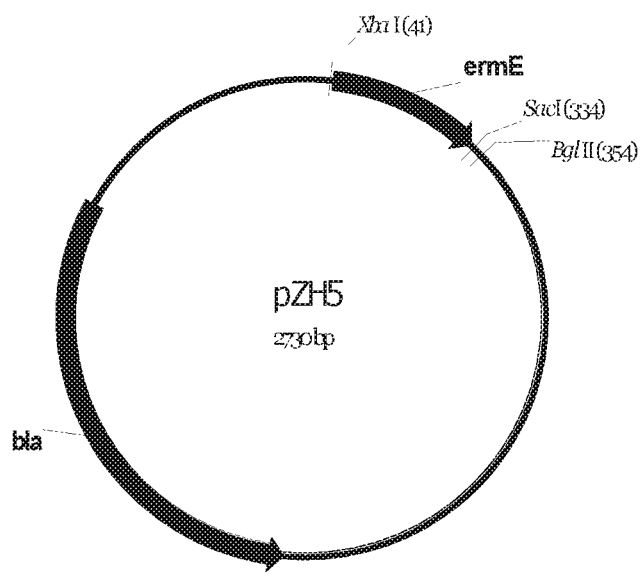
FIG. 3 is a plasmid map of pZH5, the sequence of which is set forth in SEQ ID NO: 2.

2. The doxA mutant gene fragment obtained in step 1 was digested with SacI and BglII to obtain the doxA mutant fragment 4; the vector pZH5 (FIG. 3) was digested with SacI and BglII to obtain the vector fragment 4; the doxA mutant fragment 4 was ligated with the vector fragment 4 to obtain a recombinant plasmid, which was named pZH99. In this process, the doxA mutant gene was cloned downstream of the promoter ermE*.

3. The pZH99 was digested with XbaI and BglII to obtain ermE*+doxA mutant gene fragment; the vector pSET152 was digested with XbaI and BamHI to obtain vector fragment 5; the ermE*+doxA mutant gene fragment was ligated with the vector fragment 5 to obtain a recombinant plasmid, which was named pZH100.

The sequence of the ermE* was set forth in positions 46 to 325 of SEQ ID NO: 2. pZH100 was a DoxA protein mutant-expressing plasmid.

4. Using the genomic DNA of *Streptomyces* (CGMCC No. 4827) as a template and DoxAF/DoxAR as a primer pair, the doxA gene was amplified.

The PCR amplification system and procedure were the same as in Example 1 except that the primers were different.

Using the amplified doxA gene, recombinant plasmid pZH98 was obtained through steps 2 to 3. The pZH98 was sent for sequencing and the results were in line with expectations. pZH98 was a DoxA protein-expressing plasmid, used as a control for pZH100.

Example 6—Screening of doxA Mutants

1. Construction of recombinant *E. coli* ET12567 (pUZ8002, pZH98) and ET12567 (pUZ8002, pZH100)

pZH98 and pZH100 were transformed into *E. coli* ET12567 (pUZ8002), respectively, as follows:

1 μl of the plasmid pZH98 and pZH100 prepared in Example 5 were added to 100 μl of *E. coli* ET12567 (pUZ8002) competent cells respectively, placed on ice for 30 min, heat-shocked at 42° C. for 90 sec, then rapidly placed on ice cooling for 1 min. 900 μl of liquid LB medium was added and the resulting mixture was kept in 37° C. water bath for 50 min. 100 μl of each was plated on solid LB medium containing 25 μg/ml chloramphenicol (Cm), 50 μg/ml kanamycin (Km) and 50 μg/ml Apramycin (Am), and cultured overnight at 37° C. Transformants were grown respectively, namely recombinant *E. coli* ET12567 (pUZ8002, pZH98) and ET12567 (pUZ8002, pZH100).

2. Conjugal Transfer (1) One single colony of the ET12567 (pUZ8002, pZH98) transformants obtained in step 1 is selected and then inoculated into 3 ml of liquid LB medium containing 25 μg/ml Cm, 50 μg/ml Km and 50 μg/ml Am, and cultured overnight at 37° C., 250 rpm. After that, 300 μl of the culture was inoculated into 30 ml of liquid LB medium.

(2) All the transformants of ET12567 (pUZ8002, pZH100) obtained in step 1 were washed with 1 ml of liquid LB medium and all inoculated into 30 ml of liquid LB medium containing 25 μg/ml Cm, 50 μg/ml Km and 25 μg/ml Am. The transformants were cultured at 37° C., 250 rpm for 4-6 h to an OD600 of 0.4-0.6. After centrifugation, the cells were collected, washed twice with liquid LB medium, and finally, 500 μl of liquid LB medium was added to suspend the cells for use.

(3) 50 μl of the cell suspension of ZH12 prepared in Example 3 was inoculated into 30 ml of TSB medium, and cultured at 28° C., 220 rpm for 48 hr. Then 500 μl of the culture was added to 500 μl of the ET12567 (pUZ8002, pZH98) obtained in the step (1) and the ET12567 (pUZ8002, pZH100) obtained in the step (2) respectively. 800 μl of the supernatant was removed by centrifugation. The cells were suspended in the remaining supernatant and plated on MS solid medium plates, and cultured at 28° C. for 16-20 h. Then the surface of the medium was covered with 1 ml of sterilized water containing 500 μg of apramycin (Am) and 500 μg of nalidixic acid (Nal), cultured at 28° C. for 4-8 days, and the conjugants was grown. They were named ZH98 and ZH100, respectively. The conjugants ZH98 and ZH100 were spotted onto the solid slant medium in Example 4.

3. Fermentation Test

Fermentation and HPLC detection of epirubicin of ZH98 and ZH100 was carried out in accordance with the method of Example 4.

Figure 6:
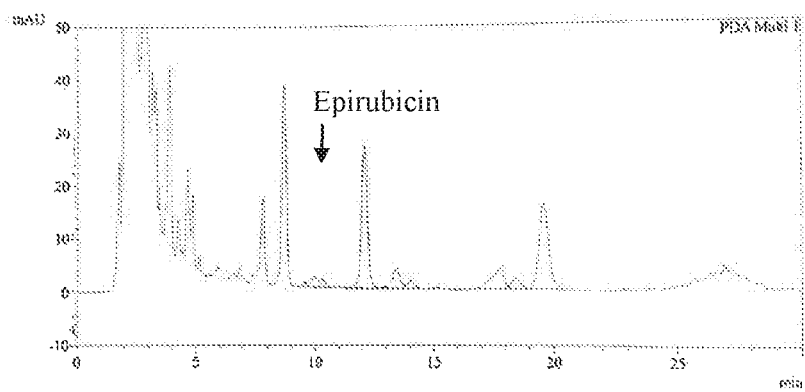
FIG. 6 is an HPLC detection spectrum of the ZH98 fermentation broth.

The HPLC detection spectrum of the ZH98 fermentation broth was shown in FIG. 6.

Figure 7:
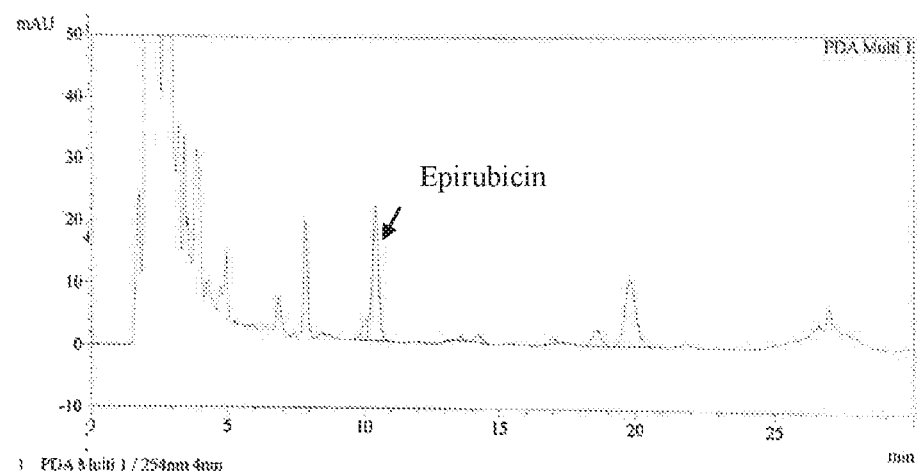
FIG. 7 is an HPLC detection spectrum of the ZH100 fermentation broth.

The HPLC detection spectrum of the ZH100 fermentation broth was shown in FIG. 7, wherein the retention time of epirubicin was 10.316 min.

Figure 8:
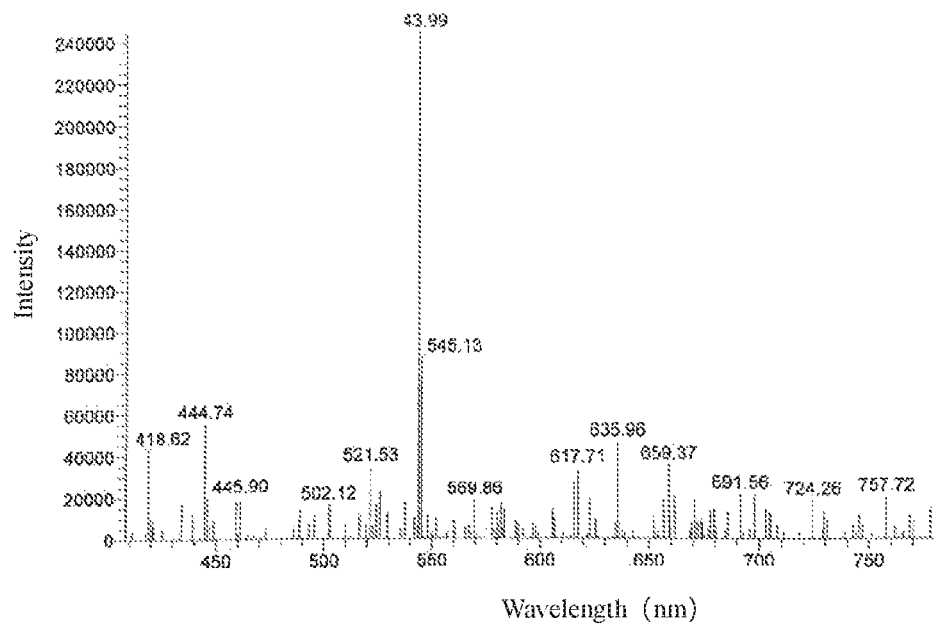
FIG. 8 is a mass spectrum of epirubicin in the ZH100 fermentation broth.

The mass spectrum of epirubicin in the ZH100 fermentation broth was shown in FIG. 8.

Using the fermentation results of ZH98 as a control, epirubicin high-producing strains of doxA mutant ZH100 were screened. One strain, whose epirubicin potency was significantly increased, was obtained. The epirubicin potency of its fermentation broth reached 102.0 µg/ml, while the control ZH98 was 0.72 µg/ml.

4. DoxA Mutation Sites Detection

The genomic DNA of the high-producing strain of ZH100 obtained in step 3 was extracted according to step 1 in Example 1. ermEF/DoxAR were used as a primer pair to carry out a PCR reaction to obtain PCR amplification products.

The sequences of the primers were as follows:

```
ermEF:
                                            (SEQ ID No. 13)
5'-AGCCCGACCCGAGCACGC-3'

DoxAR:
                                            (SEQ ID No. 14)
5'-GGAAGATCTTCAGCGCAGCCAGACGGG-3'
```

The PCR amplification products were sent for sequencing.

The sequencing results showed that the sequence of the doxA mutant gene of the strain was as set forth in SEQ ID NO: 15.

The amino acid sequence of the protein encoded by the doxA mutant gene was set forth in SEQ ID NO: 16.

The sequence of the doxA gene of *Streptomyces* (CGMCC No. 4827) was set forth in SEQ ID NO: 17.

The amino acid sequence of the DoxA protein encoded by the doxA gene of *Streptomyces* (CGMCC No. 4827) was set forth in SEQ ID NO: 18.

Sequencing revealed that the base mutations of the doxA gene in this strain were 397G>A, 399C>T, 1016C>A, and 1193G>C, and the changes of amino acid codon were 5'-GCC-3' at positions 397-399 to 5'-ACT-3', 5'-GCC-3' at positions 1015-1017 to 5'-GAC-3', and 5'-TGC-3' at positions 1192-1194 to 5'-TCC-3. Correspondingly, amino acids changed at three sites of the DoxA protein: the alanine at position 133 of DoxA protein was changed to threonine (A133T), the alanine at position 339 was changed to aspartic acid (A339D) and the cysteine at position 398 was changed to serine (C398S).

```
SEQ ID NO: 1:
5'-agcttgcatgcctgcaggtcgactctagaggatccccgggtaccgagctcgaattcatcgatgatcagat caaggcgaatacttcatatgcggggatcgaccgcgcgggtcccggacggggaagagcggggagcttgccagaga gcgacgacttcccccttgcgttggtgattgccggtcagggcagccatccgccatcgtcgcgtagggtgtcacaccccag gaatcgcgtcactgaacacagcagccggtaggacgaccatgactgagttggacaccatcgcaaatccgtccgatccc gcggtgcagcggatcatcgatgtcaccaagccgtcgcgatccaacataaagacaacgttgatcgaggacgtcgagcc cctcatgcacagcatcgcggccggggtggagttcatcgaggtctacggcagcgacagcagtccttttccatctgagttg ctggatctgtgcgggcggcagaacataccggtccgcctcatcgactcctcgatcgtcaaccagttgttcaaggggggag cggaaggccaagacattcggcatcgcccgcgtccctcgcccggccaggttcggcgatatcgcgagccggcgtggg gacgtcgtcgttctcgacggggtgaagatcgtcgggaacatcggcgcgatagtacgcacgtcgctcgcgctcggagc gtcggggatcatcctggtcgacagtgacatcaccagcatcgcggaccggcgtctccaaagggccagccgaggttacg tcttctcccttcccgtcgttctctccggtcgcgaggaggccatcgccttcattcgggacagcggtatgcagctgatgacg ctcaaggcggatggcgacatttccgtgaaggaactcggggacaatccggatcggctggccttgctgttcggcagcga aaagggtgggccttccgacctgttcgaggaggcgtcttccgcctcggtttccatcccatgatgagccagaccgagtct ctcaacgtttccgtttccctcggaatcgcgctgcacgagaggatcgacaggaatctcgcggccaaccgataagcgcct ctgttcctcggacgctcggttcctcgacctcgattcgtcagtgatgatctgccggtctccctatagtgagtcgtattaatttc gataagccaggttaacttgtttattgcagcttataatggttacaaataaagcaatagcatcacaaatttcacaaataaagcat tttttcactgcattctagttgtggtttgtccaaactcatcaatgtatcttatcatgtctggatctgacgggtgcgcatgatcgtg ctcctgtcgttgaggacccggctaggctggcggggttgccttactggttagcagaatgaatcaccgatacgcgagcga acgtgaagcgactgctgctgcaaaacgtctgcgacctgagcaacaacatgaatggtcttcggtttccgtgtttcgtaaag tctggaaacgcggaagtcagcgctcttccgcttcctcgctcactgactcgctgcgctcggtcgttcggctgcggcgagc ggtatcagctcactcaaaggcggtaatacggttatccacagaatcagggataacgcaggaaagaacatgtgagcaa aaggccagcaaaaggccagcaaaaggccaggaaccgtaaaaaggccgcgttgctggcgttttccataggctccgcc ccctgacgagcatcacaaaaatcgacgctcaagtcagaggtggcgaaacccgacaggactataaagataccaggc gtttccccctggaagctccctcgtgcgctctcctgttccgaccctgccgcttaccggataccgtccgcctttctcccttcg
```

-continued ggaagcgtggcgctttctcatagctcacgctgtaggtatctcagttcggtgtaggtcgttcgctccaagctgggctgtgtg cacgaaccccccgttcagcccgaccgctgcgccttatccggtaactatcgtcttgagtccaaccggtaagacacgact tatcgccactggcagcagccactggtaacaggattagcagagcgaggtatgtaggcggtgctacagagttcttgaagt ggtggcctaactacggctacactagaaggacagtatttggtatctgcgctctgctgaagccagttaccttcggaaaaaga gttggtagctcttgatccggcaaacaaaccaccgctggtagcggtggttttttttgtttgcaagcagcagattacgcgcaga aaaaaaggatctcaagaagatcdttgatcttttctacggggtctgacgctcagtggaacgaaaactcacgttaagggatt ttggtcatgagattatcaaaaaggatcttcacctagatccttttaaattaaaaatgaagttttaaatcaatctaaagtatatatg agtaaacttggtctgacagttaccaatgcttaatcagtgaggcacctatctcagcgatctgtctatttcgttcatccatagttg cctgactccccgtcgtgtagataactacgatacgggagggcttaccatctggccccagtgctgcaatgataccgcgaga cccacgctcaccggctccagatttatcagcaataaaccagccagccggaagggccgagcgcagaagtggtcctgca actttatccgcctccatccagtctattaattgttgccgggaagctagagtaagtagttcgccagttaatagtttgcgcaacgt tgttgccattgctgcaggcatcgtggtgtcacgctcgtcgtttggtatggcttcattcagctccggttcccaacgatcaagg cgagttacatgatccccatgttgtgcaaaaaagcggttagctccttcggtcctccgatcgttgtcagaagtaagttggcc gcagtgttatcactcatggttatggcagcactgcataattctcttactgtcatgccatccgtaagatgcttttctgtgactggt gagtactcaaccaagtcattctgagaatagtgtatgcggcgaccgagttgctcttgcccggcgtcaacacgggataata ccgcgccacatagcagaactttaaaagtgctcatcattggaaaacgttcttcggggcgaaaactctcaaggatcttaccg ctgttgagatccagttcgatgtaacccactcgtgcacccaactgatcttcagcatcttttactttcaccagcgtttctgggtg agcaaaaacaggaaggcaaaatgccgcaaaaaagggaataagggcgacacggaaatgttgaatactcatactcttcc ttttcaatattattgaagcatttatcagggttattgtctcatgagcggatacatatttgaatgtatttagaaaaataaacaaata ggggttccgcgcacatttccccgaaaagtgccacctgacgtctaagaaaccattattatcatgacattaacctataaaaat aggcgtatcacgaggccctttcgtctcgcgcgtttcggtgatgacggtgaaaacctctgacacatgcagctcccggaga cggtcacagcttgtctgtaagcggatgccgggagcagacaagcccgtcagggcgcgtcagcgggtgttggcgggtg tcggggctggcttaactatgcggcatcagagcagattgtactgagagtgcaccatatggacatattgtcgttagaacgcg gctacaattaatacataaccttatgtatcatacacatacgatttaggtgacactatagaactcgacctgcaggtccccggg gatcggtcttgccttgctcgtcggtgatgtacttcaccagctccgcgaagtcgctcttcttgatggagcgcatgggacgt gcttggcaatcacgcgcaccccccggccgttttagcggctaaaaaagtcatggctctgccctcgggcggaccacgcc catcatgaccttgccaagctcgtcctgcttctcttcgatcttcgccagcagggcgaggatcgtggcatcaccgaaccgc gccgtgcgcgggtcgtcggtgagccagagtttcagcaggccgcccaggcggcccaggtcgccattgatgcgggcca gctcgcggacgtgctcatagtccacgacgcccgtgattttgtagccctggccgacggccagcaggtaggccgacagg ctcatgccggccgccgccgcatttcctcaatcgctcttcgttcgtctggaaggcagtacaccttgataggtgggctgcc cttcctggttggcttggtttcatcagccatccgcttgccctcatctgttacgccggcggtagccggccagcctcgcagag caggattcccgttgagcaccgccaggtgcgaataagggacagtgaagaaggaacacccgctcgcgggtgggcctac ttcacctatcctgcccggctgacgccgttggatacaccaaggaaagtctacacgaaccattggcaaaatcctgtatatc gtgcgaaaaggatggatataccgaaaaaatcgctataatgaccccgaagcagggttatgcagcggaaaagatccgt cgagcagctga-3'

SEQ ID NO: 2:
5'-gaactcgagcagctgaagcttgcatgcctgcaggtcgactctagaagcccgacccgagcacgcgccggc acgcctggtcgatgtcggaccggagttcgaggtacgcggcttgcaggtccaggaaggggacgtccatgcgagtgtcc gttcgagtggcggcttgcgcccgatgctagtcgcggttgatcggcgatcgcaggtgcacgcggtcgatcttgacggct ggcgagaggtgcggggaggatctgaccgacgcggtccacacgtggcaccgcgatgctgttgtgggctggacaatcg tgccggttggtaggatccagcggtgagcgagctcgaattcatcgatgatatcagatctgccggtctccctatagtgagtc -continued

```
gtattaatttcgataagccaggttaacctgcattaatgaatcggccaacgcgcggggagaggcggtttgcgtattgggc gctcttccgcttcctcgctcactgactcgctgcgctcggtcgttcggctgcggcgagcggtatcagctcactcaaaggc ggtaatacggttatccacagaatcaggggataacgcaggaaagaacatgtgagcaaaaggccagcaaaaggccagg aaccgtaaaaaggccgcgttgctggcgtttttccataggctccgcccccctgacgagcatcacaaaaatcgacgctcaa gtcagaggtggcgaaacccgacaggactataaagataccaggcgtttccccctggaagctccctcgtgcgctctcctgt tccgacccgccgcttaccggatacctgtccgcattctcccttcgggaagcgtggcgattctcatagctcacgctgtag gtatctcagttcggtgtaggtcgttcgctccaagctgggctgtgtgcacgaaccccccgttcagcccgaccgctgcgcc ttatccggtaactatcgtcttgagtccaacccggtaagacgacttatcgccactggcagcagccactggtaacaggat tagcagagcgaggtatgtaggcggtgctacagagttcttgaagtggtggcctaactacggctacactagaagaacagt atttggtatctgcgctctgctgaagccagttac cttcggaaaaagagttggtagctcttgatccggcaaacaaaccaccg ctggtagcggtggtttttttgtttgcaagcagcagattacgcgcagaaaaaaaggatctcaagaagatcctttgatatttct acggggtctgacgctcagtggaacgaaaactcacgttaagggattttggtcatgagattatcaaaaaggatcttaccta gatcatttaaattaaaaatgaagttttaaatcaatctaaagtatatatgagtaaacttggtctgacagttaccaatgcttaatc agtgaggcacctatctcagcgatctgtctatttcgttcatccatagttgcctgactccccgtcgtgtagataactacgatac gggagggcttaccatctggccccagtgctgcaatgataccgcgagacccacgctcaccggctccagatttatcagcaa taaaccagccagccggaagggccgagcgcagaagtggtcctgcaactttatccgcctccatccagtctattaattgttgc cgggaagctagagtaagtagttcgccagttaatagtttgcgcaacgttgttgccattgctacaggcatcgtggtgtcacg ctcgtcgtttggtatggcttcattcagctccggttcccaacgatcaaggcgagttacatgatcccccatgttgtgcaaaaaa gcggttagctccttcggtcctccgatcgttgtcagaagtaagttggccgcagtgttatcactcatggttatggcagcactg cataattctcttactgtcatgccatccgtaagatgcttttctgtgactggtgagtactcaaccaagtcattctgagaatagtgt atgcggcgaccgagttgctcttgcccggcgtcaatacgggataataccgcgccacatagcagaactttaaaagtgctca tcattggaaaacgttcttcggggcgaaaactctcaaggatcttaccgctgttgagatccagttcgatgtaacccactcgtg cacccaactgatcttcagcatattactttcaccagcgtttctgggtgagcaaaaacaggaaggcaaaatgccgcaaaa aagggaataagggcgacacggaaatgttgaatactcatactcttcctttttcaatattattgaagcatttatcagggttattgt ctcatgagcggatacatatttgaatgtatttagaaaaataaacaaataggggttccgcgcacatttccccgaaaagtgcca cctgacgtctaagaaaccattattatcatgacattaacctataaaaataggcgtatcacgaggccattcgtctcgcgcgtt tcggtgatgacggtgaaaacctctgacacatgcagctcccggagacggtcacagcttgtctgtaagcggatgccggga gcagacaagcccgtcagggcgcgtcagcgggtgttggcgggtgtcggggctggcttaactatgcggcatcagagca gattgtactgagagtgcaccatatggacatattgtcgttagaacgcggctacaattaatacataaccttatgtatcatacac atacgatttaggtgacactata-3'
```

SEQ ID NO: 9:
```
5'-atgcgggtcgtggttctgggggcgacgggcagcgtcggtcggcaggtgtgtgcggcgtaccaggcgca cgggtgggacgtgcacggggtggcccgccgcccggcgccgcacctgagcgggtgcgggttcacggagctggacc tcgcggccgccgcgcctgggcggatcgccacggtgctgggtgatcttccggcggacgtcgtggtcaacgcggcggg cggctggggcgacaccgaggaggagatgacgtactcgcatctgcgactggtgcgacgcctggtggaggcgctcgc gctgctcccgttccggcccggctggtccatctgggtcggtgcacgagtacggtcccgtgccggccggcacgctgc tgcacgaggacctgctgccggagccggtcacgccgtacgcgcgcgtcaaactggagacctcgtcggccgtcctgac cgcagcgcgggccggtgtcctggacgcggtggtgctgcgcgcggcgaacatgtcgggcccgcatccgccgcagga gagtttcctggccgccctgatggcgcgtatcagcacggcattcgcgcacggtgggcggctggagttgagcgtcgcgg acgcacggcgggacttcatcgacgtgcgggacgtcgcacaggcggtggtgcgtgccgggcgggctccggcggtcg gcgggctggtcgtcaacatcgggcgcggggacgccgtgccgatcggtgatctggtcggctggctgctggaggccgc
```

-continued cgccttcccggaggaccgggtcgaccgccgggaggcgccggtgcggagcaagggcggcgactggacccggctg gacatcgggcgggcccggcggttgctgtcctgggcgccgcgcatcggcctgcgggactccgtccacagcatgtggc ggaccgcgcacggcgccccggcctag-3'

SEQ ID NO: 10:
5'-atggggcggttttcggtgtgcccgccccggccgaccggaatactgaagagcatgctgacgactgggatgt gcgaccgaccgctggtcgtcgtactcggagcctccggctatatcgggtcggccgtcgcggcggaactcgcccggtg gccggtcctgttgcggctggtggcccggcgaccgggcgtcgttccgccgggcggcgccgcggagaccgagacgc gtacggccgacctgacggcggcgagcgaggtcgccctcgccgtgacggacgccgacgtggtgatccacctggtcg cgcgcctcacccagggagcggcatggcgggcggcggagagcgatccggtggccgagcgggtgaacgtcggggt gatgcacgacgtcgtcgcggccctgcggtccgggcgccgcgccgggccgcccccggtggtggtgttcgccgggtc ggtctaccaggtgggccgcccgggtcgggtcgacggcagtgagccggacgagcccgtgacggcctatgcccgtca gaaactcgacgccgaacggacgttgaagtccgccacggtcgagggtgtcctgcgggggatctcgctgcggctgccc accgtctacggcgcggggccgggcccgcagggcaacggcgtcgtgcaggcgatggtgctccgggcgctcgccga cgaggccctcaccgtgtggaacggaagcgtggtggagcgtgacctggtgcatgtggaggatgtcgcgcaggccttc gtgagctgcctggcgcacgcggatgcgctcgccgggcggcactggctgctcggcagcggtcgtcctgtgaccgtcc cgcacctcttcggtgccatcgccgccggcgtgtccgcccgcaccgggcgccccgcggtgcccgtgaccgcggtgga ccctccggcgatggcgacggcggcggacttccacgggaccgtcgtcgactcctcggcgttccgcgcggtcaccggg tggcggccgcggctgtcgcttcaggagggcctggaccacatggtggcggcttacgtgtag-3'

SEQ ID NO: 15:
5'-gtggccgtcgacccgttcgcgtgtcccatgatgaccatgcagcgcaagcccgaggtgcacgacgccttcc gggaggcgggcccggtcgtcgaggtgaacgccccgcgggcggacccgcctgggtcatcaccgatgacgccctc gcccgcgaggtgctggccgatccccggttcgtgaaggaccccgacctcgcccccgccgcctggcgggggtggac gacggtctcgacatccccgttccggagctgcgtccgttcacgctcatcgccgtggacggcgaggcccaccggcgcct gcgccgcatccacgcacctgcgttcaacccgcgccggctggccgagcggacggatcgcatcgccgcgatcgccgg ccggctgctcaccgaactcgccgacacttccggccggtcgggcaaaccggccgagctgatcggcggcttcgcgtac cacttcccgctgttggtcatctgcgagctgctcggtgtgccggtcaccgatccggcgatggcccgcgaggccgtcagc gttctcaaggcactcggcctcggcggcccgcagagcggcgggggtgacggcacggaccctgccgggggcgtgcc ggacacctcggcccctggagagcctgctcctcgaagccgtgcactcagcccggcgaacgacaccccgaccatgacc cgcgtgctgtacgagcgcgcgcaggccgagttcggctcggtctccgacgaccagctcgtctacatgatcaccgggct catcttcgccgccacgacaccaccggctccttcctgggcttcctgctcgcggaggtcctggcgggccgcctcgcgg cggatgccgacgaggacgccgtctcccggttcgtggaggaggcgctgcgctaccaccgccggtgccctacacgtt gtggaggttcgctgccacggaggtgaccatcggcggcgtccggctgccccgcggagcgccggtgctggtggacatc gagggcaccaacaccgacggccgccatcacgacgacccgcacgccttccacccggaccgtccctcgtggcggcgg ctcacccttcggcgacgggccgcactactgcatcggggagcagctcgcccagctggagtcgcgcacgatgatcggcg tactgcgcagcaggttccccgaggcccgactggccgtgccgtacgacgagttgcggtggtcccggaaggggccca gacggcgcggctcaccgaactgcccgtctggctgcgctga-3'

SEQ ID NO: 16:
VAVDPFACPMMTMQRKPEVHDAFREAGPVVEVNAPAGGPAWVITDDALA

REVLADPRFVKDPDLAPAAWRGVDDGLDIPVPELRPFTLIAVDGEAHRRLR

RIHAPAFNPRRLAERTDRIAAIAGRLLTELADTSGRSGKPAELIGGFAYHFPL

LVICELLGVPVTDPAMAREAVSVLKALGLGGPQSGGGDGTDPAGGVPDTS

ALESLLLEAVHSARRNDTPTMTRVLYERAQAEFGSVSDDQLVYMITGLIFA

-continued

GHDTTGSFLGFLLAEVLAGRLAADADEDAVSRFVEEALRYHPPVPYTLWR

FAATEVTIGGVRLPRGAPVLVDIEGTNTDGRHHDDPHAFHPDRPSWRRLTF

GDGPHYCIGEQLAQLESRTMIGVLRSRFPEARLAVPYDELRWSRKGAQTA

RLTELPVWLR

SEQ ID NO: 17:
5'-gtggccgtcgacccgttcgcgtgtcccatgatgaccatgcagcgcaagcccgaggtgcacgacgccttcc ggaggcgggcccggtcgtcgaggtgaacgccccgcgggcggacccgcctgggtcatcaccgatgacgccctc gcccgcgaggtgctggccgatccccggttcgtgaaggaccccgacctcgcccccgccgcctggcgggggtggac gacggtctcgacatccccgttccggagctgcgtccgttcacgctcatcgccgtggacggcgaggccaccggcgcct gcgccgcatccacgcacctgcgttcaacccgcgccggctggccgagcggacggatcgcatcgccgcgatcgccgg ccggctgctcaccgaactcgccgacgcctccggccggtcgggcaaaccggccgagctgatcggcggcttcgcgtac cacttcccgctgttggtcatctgcgagctgctcggtgtgccggtcaccgatccggcgatgggcccgcgaggccgtcagc gttctcaaggcactcggcctcggcggcccgcagagcggcgggggtgacggcacggaccctgccggggggcgtgcc ggacacctcggccctggagagcctgctcctcgaagccgtgcactcagcccggcggaacgacaccccgaccatgacc cgcgtgctgtacgagcgcgcgcaggccgagttcggctcggtctccgacgaccagctcgtctacatgatcaccgggct catcttcgccggccacgacaccaccggctccttcctgggcttcctgctcgcggaggtcctggcgggccgcctcgcgg cggatgccgacgaggacgccgtctcccggttcgtggaggaggcgctgcgctaccaccgccggtgccctacacgtt gtggaggttcgctgccacggaggtgaccatcggcggcgtccggctgccccgcggagcgccggtgctggtggacatc gagggcaccaacaccgacggccgccatcacgacgccccgcacgccttccacccggaccgtccctcgtggcggcgg ctcaccttcggcgacgggccgcactactgcatcggggagcagctcgcccagctggagtcgcgcacgatgatcggcg tactgcgcagcaggttccccgaggcccgactggccgtgccgtacgacgagttgcggtggtgccggaaggggggccca gacggcgcggctcaccgaactgcccgtctggctgcgctga-3'

SEQ ID NO: 18:
VAVDPFACPMMTMQRKPEVHDAFREAGPVVEVNAPAGGPAWVITDDALA

REVLADPRFVKDPDLAPAAWRGVDDGLDIPVPELRPFTLIAVDGEAHRRLR

RIHAPAFNPRRLAERTDRIAAIAGRLLTELADASGRSGKPAELIGGFAYHFP

LLVICELLGVPVTDPAMAREAVSVLKALGLGGPQSGGGDGTDPAGGVPDT

SALESLLLEAVHSARRNDTPTMTRVLYERAQAEFGSVSDDQLVYMITGLIF

AGHDTTGSFLGFLLAEVLAGRLAADADEDAVSRFVEEALRYHPPVPYTLW

RFAATEVTIGGVRLPRGAPVLVDIEGTNTDGRHHDAPHAFHPDRPSWRRLT

FGDGPHYCIGEQLAQLESRTMIGVLRSRFPEARLAVPYDELRWCRKGAQT

ARLTELPVWLR

---

The invention claimed is:

1. A DoxA protein variant comprising the amino acid sequence set forth in SEQ ID NO: 18 with amino acid substitutions Ala133Thr, Ala339Asp, and Cys398Ser, wherein said DoxA protein variant is capable of converting epidaunorubicin to epirubicin.

2. The DoxA protein variant of claim 1, said DoxA protein variant comprising the amino acid sequence set forth in SEQ ID NO: 16.

3. The DoxA protein variant of claim 1, said DoxA protein variant consisting of the amino acid sequence set forth in SEQ ID NO: 16.

4. A nucleic acid molecule encoding the DoxA protein variant of claim 1.

5. The nucleic acid molecule of claim 4, wherein the nucleic acid molecule comprises the nucleic acid sequence set forth in SEQ ID NO: 15.

6. An expression cassette comprising the nucleic acid molecule of claim 4.

7. A recombinant vector comprising the nucleic acid molecule of claim 4.

8. A microorganism comprising the recombinant vector of claim 7.

9. A transgenic cell line comprising the recombinant vector of claim 7.

10. A method for constructing an epirubicin-expressing *Streptomyces* cell, said method comprising the steps of:
   1) replacing the dnmV gene of a starting *Streptomyces* cell in situ with avrE gene, and
   2) mutating the doxA gene of the starting *Streptomyces* cell into a gene sequence encoding the DoxA protein variant set forth in SEQ ID NO: 16.

11. The method according to claim 10, wherein the sequence of the dnmV gene is set forth in SEQ ID NO: 9; the sequence of the avrE gene is set forth in SEQ ID NO: 10; the doxA gene sequence is set forth in SEQ ID NO: 15.

12. A *Streptomyces* cell produced by the method of claim 10.

13. A method for preparing epirubicin, said method comprising culturing the *Streptomyces* cell of claim 12 in fermentation medium under conditions wherein the epirubicin is produced.

* * * * *

SEQUENCE LISTING

<160> NUMBER OF SEQ ID NOS: 18

<210> SEQ ID NO 1
<211> LENGTH: 4610
<212> TYPE: DNA
<213> ORGANISM: Artificial sequence
<220> FEATURE:
<223> OTHER INFORMATION: pHY642

<400> SEQUENCE: 1
agcttgcatg cctgcaggtc gactctagag gatccccggg taccgagctc gaattcatcg    60

-continued

| | |
|---|---|
| atgatatcag atcaaggcga atacttcata tgcggggatc gaccgcgcgg gtcccggacg | 120 |
| gggaagagcg gggagctttg ccagagagcg acgacttccc cttgcgttgg tgattgccgg | 180 |
| tcagggcagc catccgccat cgtcgcgtag ggtgtcacac cccaggaatc gcgtcactga | 240 |
| acacagcagc cggtaggacg accatgactg agttggacac catcgcaaat ccgtccgatc | 300 |
| ccgcggtgca gcggatcatc gatgtcacca agccgtcgcg atccaacata aagacaacgt | 360 |
| tgatcgagga cgtcgagccc ctcatgcaca gcatcgcggc cggggtggag ttcatcgagg | 420 |
| tctacggcag cgacagcagt cctttccat ctgagttgct ggatctgtgc gggcggcaga | 480 |
| acataccggt ccgcctcatc gactcctcga tcgtcaacca gttgttcaag ggggagcgga | 540 |
| aggccaagac attcggcatc gcccgcgtcc ctcgcccggc caggttcggc gatatcgcga | 600 |
| gccggcgtgg ggacgtcgtc gttctcgacg gggtgaagat cgtcgggaac atcgcgcga | 660 |
| tagtacgcac gtcgctcgcg ctcggagcgt cggggatcat cctggtcgac agtgacatca | 720 |
| ccagcatcgc ggaccggcgt ctccaaaggg ccagccgagg ttacgtcttc tcccttcccg | 780 |
| tcgttctctc cggtcgcgag gaggccatcg ccttcattcg ggacagcggt atgcagctga | 840 |
| tgacgctcaa gcggatggc gacatttccg tgaaggaact cggggacaat ccggatcggc | 900 |
| tggccttgct gttcggcagc gaaaagggtg ggccttccga cctgttcgag gaggcgtctt | 960 |
| ccgcctcggt ttccatcccc atgatgagcc agaccgagtc tctcaacgtt tccgtttccc | 1020 |
| tcggaatcgc gctgcacgag aggatcgaca ggaatctcgc ggccaaccga taagcgcctc | 1080 |
| tgttcctcgg acgctcggtt cctcgacctc gattcgtcag tgatgatctg ccggtctccc | 1140 |
| tatagtgagt cgtattaatt tcgataagcc aggttaactt gtttattgca gcttataatg | 1200 |
| gttacaaata aagcaatagc atcacaaatt tcacaaataa agcattttt tcactgcatt | 1260 |
| ctagttgtg tttgtccaaa ctcatcaatg tatcttatca tgtctggatc tgacgggtgc | 1320 |
| gcatgatcgt gctcctgtcg ttgaggaccc ggctaggctg gcggggttgc cttactggtt | 1380 |
| agcagaatga atcaccgata cgcgagcgaa cgtgaagcga ctgctgctgc aaaacgtctg | 1440 |
| cgacctgagc aacaacatga atggtcttcg gtttccgtgt ttcgtaaagt ctggaaacgc | 1500 |
| ggaagtcagc gctcttccgc ttcctcgctc actgactcgc tgcgctcggt cgttcggctg | 1560 |
| cggcgagcgg tatcagctca ctcaaaggcg gtaatacggt tatccacaga atcaggggat | 1620 |
| aacgcaggaa agaacatgtg agcaaaaggc cagcaaaagg ccaggaacc | 1680 |
| gtaaaaaggc cgcgttgctg gcgttttcc ataggctccg ccccctgac gagcatcaca | 1740 |
| aaaatcgacg ctcaagtcag aggtggcgaa acccgacagg actataaaga taccaggcgt | 1800 |
| ttccccctgg aagctccctc gtgcgctctc ctgttccgac cctgccgctt accggatacc | 1860 |
| tgtccgcctt tctcccttcg ggaagcgtgg cgctttctca tagctcacgc tgtaggtatc | 1920 |
| tcagttcggt gtaggtcgtt cgctccaagc tgggctgtgt gcacgaaccc cccgttcagc | 1980 |
| ccgaccgctg cgccttatcc ggtaactatc gtcttgagtc aacccggta agacacgact | 2040 |
| tatcgccact ggcagcagcc actggtaaca ggattagcag agcgaggtat gtaggcggtg | 2100 |
| ctacagagtt cttgaagtgg tggcctaact acggctacac tagaaggaca gtatttggta | 2160 |
| tctgcgctct gctgaagcca gttaccttcg gaaaaagagt tggtagctct tgatccggca | 2220 |
| aacaaaccac cgctggtagc ggtggttttt tgtttgcaa gcagcagatt acgcgcagaa | 2280 |
| aaaaaggatc tcaagaagat cctttgatct tttctacggg gtctgacgct cagtggaacg | 2340 |
| aaaactcacg ttaagggatt ttggtcatga gattatcaaa aaggatcttc acctagatcc | 2400 |
| ttttaaatta aaaatgaagt tttaaatcaa tctaaagtat atatgagtaa acttggtctg | 2460 |

```
acagttacca atgcttaatc agtgaggcac ctatctcagc gatctgtcta tttcgttcat    2520
ccatagttgc ctgactcccc gtcgtgtaga taactacgat acgggagggc ttaccatctg    2580
gccccagtgc tgcaatgata ccgcgagacc cacgctcacc ggctccagat ttatcagcaa    2640
taaaccagcc agccggaagg gccgagcgca gaagtggtcc tgcaacttta tccgcctcca    2700
tccagtctat taattgttgc cgggaagcta gagtaagtag ttcgccagtt aatagtttgc    2760
gcaacgttgt tgccattgct gcaggcatcg tggtgtcacg ctcgtcgttt ggtatggctt    2820
cattcagctc cggttcccaa cgatcaaggc gagttacatg atcccccatg ttgtgcaaaa    2880
aagcggttag ctccttcggt cctccgatcg ttgtcagaag taagttggcc gcagtgttat    2940
cactcatggt tatggcagca ctgcataatt ctcttactgt catgccatcc gtaagatgct    3000
tttctgtgac tggtgagtac tcaaccaagt cattctgaga atagtgtatg cggcgaccga    3060
gttgctcttg cccggcgtca acacgggata ataccgcgcc acatagcaga actttaaaag    3120
tgctcatcat tggaaaacgt tcttcggggc gaaaactctc aaggatctta ccgctgttga    3180
gatccagttc gatgtaaccc actcgtgcac ccaactgatc ttcagcatct tttactttca    3240
ccagcgtttc tgggtgagca aaaacaggaa ggcaaaatgc cgcaaaaaag ggaataaggg    3300
cgacacggaa atgttgaata ctcatactct tcctttttca atattattga agcatttatc    3360
agggttattg tctcatgagc ggatacatat ttgaatgtat ttagaaaaat aaacaaatag    3420
gggttccgcg cacatttccc cgaaaagtgc cacctgacgt ctaagaaacc attattatca    3480
tgacattaac ctataaaaat aggcgtatca cgaggccctt tcgtctcgcg cgtttcggtg    3540
atgacggtga aaacctctga cacatgcagc tcccggagac ggtcacagct tgtctgtaag    3600
cggatgccgg gagcagacaa gcccgtcagg gcgcgtcagc gggtgttggc gggtgtcggg    3660
gctggcttaa ctatgcggca tcagagcaga ttgtactgag agtgcaccat atggacatat    3720
tgtcgttaga acgcggctac aattaataca taaccttatg tatcatacac atacgattta    3780
ggtgacacta tagaactcga cctgcaggtc cccggggatc ggtcttgcct tgctcgtcgg    3840
tgatgtactt caccagctcc gcgaagtcgc tcttcttgat ggagcgcatg ggacgcgtgct   3900 tggcaatcac gcgcaccccc cggccgtttt agcggctaaa aaagtcatgg ctctgccctc    3960
gggcggacca cgcccatcat gaccttgcca agctcgtcct gcttctcttc gatcttcgcc    4020
agcagggcga ggatcgtggc atcaccgaac gcgccgtgc gcgggtcgtc ggtgagccag    4080
agtttcagca ggccgcccag gcggcccagg tcgccattga tgcgggccag ctcgcggacg    4140
tgctcatagt ccacgacgcc cgtgattttg tagccctggc cgacggccag caggtaggcc    4200
gacaggctca tgccggccgc cgccgccttt tcctcaatcg ctcttcgttc gtctggaagg    4260
cagtacacct tgataggtgg gctgcccttc ctggttggct tggtttcatc agccatccgc    4320
ttgccctcat ctgttacgcc ggcggtagcc ggccagcctc gcagagcagg attcccgttg    4380
agcaccgcca ggtgcgaata agggacagtg aagaaggaac accgctcgc gggtgggcct    4440 acttcaccta tcctgcccgg ctgacgccgt tggatacacc aaggaaagtc tacacgaacc    4500
ctttggcaaa atcctgtata tcgtgcgaaa aaggatggat ataccgaaaa aatcgctata    4560
atgaccccga agcagggtta tgcagcggaa aagatccgtc gagcagctga              4610

<210> SEQ ID NO 2
<211> LENGTH: 2730
<212> TYPE: DNA
<213> ORGANISM: Artificial sequence
<220> FEATURE:
```

<223> OTHER INFORMATION: pZH5

<400> SEQUENCE: 2

```
gaactcgagc agctgaagct tgcatgcctg caggtcgact ctagaagccc gacccgagca      60
cgcgccggca cgcctggtcg atgtcggacc ggagttcgag gtacgcggct tgcaggtcca     120
ggaaggggac gtccatgcga gtgtccgttc gagtggcggc ttgcgcccga tgctagtcgc     180
ggttgatcgg cgatcgcagg tgcacgcggt cgatcttgac ggctggcgag aggtgcgggg     240
aggatctgac cgacgcggtc cacacgtggc accgcgatgc tgttgtgggc tggacaatcg     300
tgccggttgg taggatccag cggtgagcga gctcgaattc atcgatgata tcagatctgc     360
cggtctccct atagtgagtc gtattaattt cgataagcca ggttaacctg cattaatgaa     420
tcggccaacg cgcggggaga ggcggtttgc gtattgggcg ctcttccgct tcctcgctca     480
ctgactcgct gcgctcggtc gttcggctgc ggcgagcggt atcagctcac tcaaaggcgg     540
taatacggtt atccacagaa tcaggggata acgcaggaaa gaacatgtga gcaaaaggcc     600
agcaaaaggc caggaaccgt aaaaaggccg cgttgctggc gttttccat aggctccgcc      660
cccctgacga gcatcacaaa aatcgacgct caagtcagag gtggcgaaac ccgacaggac     720
tataaagata ccaggcgttt cccctggaa gctccctcgt gcgctctcct gttccgaccc      780
tgccgcttac cggatacctg tccgccttc tcccttcggg aagcgtggcg ctttctcata      840
gctcacgctg taggtatctc agttcggtgt aggtcgttcg ctccaagctg gctgtgtgc      900
acgaaccccc cgttcagccc gaccgctgcg ccttatccgg taactatcgt cttgagtcca     960
acccggtaag acacgactta cgccactgg cagcagccac tggtaacagg attagcagag     1020
cgaggtatgt aggcggtgct acagagttct tgaagtggtg cctaactac ggctacacta     1080
gaagaacagt atttggtatc tgcgctctgc tgaagccagt taccttcgga aaaagagttg     1140
gtagctcttg atccggcaaa caaccaccg ctggtagcgg tggtttttttt gtttgcaagc     1200
agcagattac gcgcagaaaa aaaggatctc aagaagatcc tttgatcttt tctacggggt     1260
ctgacgctca gtggaacgaa aactcacgtt aagggatttt ggtcatgaga ttatcaaaaa     1320
ggatcttcac ctagatcctt ttaaattaaa aatgaagttt taaatcaatc taagtatat     1380
atgagtaaac ttggtctgac agttaccaat gcttaatcag tgaggcacct atctcagcga     1440
tctgtctatt tcgttcatcc atagttgcct gactccccgt cgtgtagata actacgatac     1500
gggagggctt accatctggc cccagtgctg caatgatacc gcgagaccca cgctcaccgg     1560
ctccagattt atcagcaata aaccagccag ccggaagggc cgagcgcaga agtggtcctg     1620
caactttatc cgcctccatc cagtctatta attgttgccg ggaagctaga gtaagtagtt     1680
cgccagttaa tagtttgcgc aacgttgttg ccattgctac aggcatcgtg gtgtcacgct     1740
cgtcgtttgg tatggcttca ttcagctccg gttcccaacg atcaaggcga gttacatgat     1800
cccccatgtt gtgcaaaaaa gcggttagct ccttcggtcc tccgatcgtt gtcagaagta     1860
agttggccgc agtgttatca ctcatggtta tggcagcact gcataattct cttactgtca     1920
tgccatccgt aagatgcttt tctgtgactg gtgagtactc aaccaagtca ttctgagaat     1980
agtgtatgcg gcgaccgagt tgctcttgcc cggcgtcaat acgggataat accgcgccac     2040
atagcagaac tttaaaagtg ctcatcattg gaaaacgttc ttcggggcga aaactctcaa     2100
ggatcttacc gctgttgaga tccagttcga tgtaacccac tcgtgcaccc aactgatctt     2160
cagcatcttt tactttcacc agcgtttctg ggtgagcaaa acaggaagg caaaatgccg      2220
caaaaaaggg aataagggcg acacggaaat gttgaatact catactcttc cttttttcaat    2280
```

```
attattgaag catttatcag ggttattgtc tcatgagcgg atacatattt gaatgtattt    2340
agaaaaataa acaaataggg gttccgcgca catttccccg aaaagtgcca cctgacgtct    2400
aagaaaccat tattatcatg acattaacct ataaaaatag gcgtatcacg aggccctttc    2460
gtctcgcgcg tttcggtgat gacggtgaaa acctctgaca catgcagctc ccggagacgg    2520
tcacagcttg tctgtaagcg gatgccggga gcagacaagc ccgtcagggc gcgtcagcgg    2580
gtgttggcgg gtgtcggggc tggcttaact atgcggcatc agagcagatt gtactgagag    2640
tgcaccatat ggacatattg tcgttagaac gcggctacaa ttaatacata accttatgta    2700
tcatacacat acgatttagg tgacactata                                     2730
```

```
<210> SEQ ID NO 3
<211> LENGTH: 31
<212> TYPE: DNA
<213> ORGANISM: Artificial sequence
<220> FEATURE:
<223> OTHER INFORMATION: Primer DnmVLF

<400> SEQUENCE: 3
cccaagcttc cactctgccc gtccacctct t                                   31

<210> SEQ ID NO 4
<211> LENGTH: 27
<212> TYPE: DNA
<213> ORGANISM: Artificial sequence
<220> FEATURE:
<223> OTHER INFORMATION: Primer DnmVLR

<400> SEQUENCE: 4
tgctctagac tcaccegtct ccgcgtg                                        27

<210> SEQ ID NO 5
<211> LENGTH: 29
<212> TYPE: DNA
<213> ORGANISM: Artificial sequence
<220> FEATURE:
<223> OTHER INFORMATION: Primer DnmVRF

<400> SEQUENCE: 5
tgctctagac gggctggtcg tcaacatcg                                      29

<210> SEQ ID NO 6
<211> LENGTH: 29
<212> TYPE: DNA
<213> ORGANISM: Artificial sequence
<220> FEATURE:
<223> OTHER INFORMATION: Primer DnmVRR

<400> SEQUENCE: 6
ccggaattcg ctccttcctg ggcttcctg                                      29

<210> SEQ ID NO 7
<211> LENGTH: 44
<212> TYPE: DNA
<213> ORGANISM: Artificial sequence
<220> FEATURE:
<223> OTHER INFORMATION: Primer avrEF

<400> SEQUENCE: 7
acgcggagac gggtgaggcg gacatggggc ggttttcggt gtgc                     44

<210> SEQ ID NO 8
```

```
<211> LENGTH: 41
<212> TYPE: DNA
<213> ORGANISM: Artificial sequence
<220> FEATURE:
<223> OTHER INFORMATION: Primer avrER

<400> SEQUENCE: 8
gtcgtcggaa gcctgtgagc tacacgtaag ccgccaccat g         41

<210> SEQ ID NO 9
<211> LENGTH: 924
<212> TYPE: DNA
<213> ORGANISM: Artificial sequence
<220> FEATURE:
<223> OTHER INFORMATION: dnmV gene

<400> SEQUENCE: 9
atgcgggtcg tggttctggg ggcgacgggc agcgtcggtc ggcaggtgtg tgcggcgtac    60
caggcgcacg ggtgggacgt gcacggggtg gcccgccgcc cggcgccgca cctgagcggg   120
tgcgggttca cggagctgga cctcgcgccc ccgcgcctg gcggatcgc acggtgctg     180
ggtgatcttc cggcggacgt cgtggtcaac gcggcgggcg ctggggcga caccgaggag    240
gagatgacgt actcgcatct gcgactggtg cgacgcctgg tggaggcgct cgcgctgctc    300
ccgttccggc cccggctggt ccatctgggg tcggtgcacg agtacggtcc cgtgccggcc    360
ggcacgctgc tgcacgagga cctgctgccg gagccggtca cgccgtacgc gcgcgtcaaa    420
ctggagacct cgtcggccgt cctgaccgca gcgcgggccg gtgtcctgga cgcggtggtg    480
ctgcgcgcg cgaacatgtc gggcccgcat ccgccgcagg agagtttcct ggccgccctg    540
atggcgcgta tcagcacggc attcgcgcac ggtgggcggc tggagttgag cgtcgcggac    600
gcacggcggg acttcatcga cgtgcgggac gtcgcacagg cggtggtgcg tgccgggcgg    660
gctccggcgg tcggcgggct ggtcgtcaac atcgggcgcg gggacgccgt gccgatcggt    720
gatctggtcg gctggctgct ggaggccgcc gccttcccgg aggaccgggt cgaccgccgg    780
gaggcgccgg tgcggagcaa gggcggcgac tggacccggc tggacatcgg gcgggcccgg    840
cggttgctgt cctgggcgcc gcgcatcggc ctgcgggact ccgtccacag catgtggcgg    900
accgcgcacg gcgccccggc ctag                                         924

<210> SEQ ID NO 10
<211> LENGTH: 1032
<212> TYPE: DNA
<213> ORGANISM: Artificial sequence
<220> FEATURE:
<223> OTHER INFORMATION: avrE gene

<400> SEQUENCE: 10
atggggcggt tttcggtgtg cccgccccgg ccgaccggaa tactgaagag catgctgacg    60
actgggatgt gcgaccgacc gctggtcgtc gtactcggag cctccggcta tatcgggtcg   120
gccgtcgcgg cggaactcgc ccggtggccg gtcctgttgc ggctggtggc ccggcgaccg   180
ggcgtcgttc cgccgggcgg cgccgcggag accgagacgc gtacggccga cctgacggcg   240
gcgagcgagg tcgccctcgc cgtgacggac ccgacgtgg tgatccacct ggtcgcgcgc   300
ctcacccagg gagcggcatg gcgggcggcg gagagcgatc cggtggccga gcgggtgaac   360
gtcggggtga tgcacgacgt cgtcgcggcc ctgcggtccg ggcgccgcgc cgggccgccc   420
ccggtggtgg tgttcgccgg gtcggtctac caggtgggcc gccgggtcg ggtcgacggc   480
agtgagccgg acgagcccgt gacggcctat gcccgtcaga aactcgacgc cgaacggacg   540
```

```
ttgaagtccg ccacggtcga gggtgtcctg cggggatct cgctgcggct gcccaccgtc      600
tacggcgcgg ggccgggccc gcagggcaac ggcgtcgtgc aggcgatggt gctccgggcg      660
ctcgccgacg aggccctcac cgtgtggaac ggaagcgtgg tggagcgtga cctggtgcat      720
gtggaggatg tcgcgcaggc cttcgtgagc tgcctggcgc acgcggatgc gctcgccggg      780
cggcactggc tgctcggcag cggtcgtcct gtgaccgtcc cgcacctctt cggtgccatc      840
gccgccggcg tgtccgcccg caccgggcgc ccgcggtgc ccgtgaccgc ggtggaccct       900
ccggcgatgg cgacggcggc ggacttccac gggaccgtcg tcgactcctc ggcgttccgc      960
gcggtcaccg gtggcggcc gcggctgtcg cttcaggagg gcctggacca catggtggcg      1020
gcttacgtgt ag                                                         1032
```

<210> SEQ ID NO 11
<211> LENGTH: 27
<212> TYPE: DNA
<213> ORGANISM: Artificial sequence
<220> FEATURE:
<223> OTHER INFORMATION: Primer DoxAF

<400> SEQUENCE: 11

```
acagagctcg tggccgtcga cccgttc                                          27
```

<210> SEQ ID NO 12
<211> LENGTH: 27
<212> TYPE: DNA
<213> ORGANISM: Artificial sequence
<220> FEATURE:
<223> OTHER INFORMATION: Primer DoxAR

<400> SEQUENCE: 12

```
ggaagatctt cagcgcagcc agacggg                                          27
```

<210> SEQ ID NO 13
<211> LENGTH: 18
<212> TYPE: DNA
<213> ORGANISM: Artificial sequence
<220> FEATURE:
<223> OTHER INFORMATION: Primer ermEF

<400> SEQUENCE: 13

```
agcccgaccc gagcacgc                                                    18
```

<210> SEQ ID NO 14
<211> LENGTH: 27
<212> TYPE: DNA
<213> ORGANISM: Artificial sequence
<220> FEATURE:
<223> OTHER INFORMATION: Primer DoxAR

<400> SEQUENCE: 14

```
ggaagatctt cagcgcagcc agacggg                                          27
```

<210> SEQ ID NO 15
<211> LENGTH: 1248
<212> TYPE: DNA
<213> ORGANISM: Artificial sequence
<220> FEATURE:
<223> OTHER INFORMATION: doxA mutant gene

<400> SEQUENCE: 15

```
gtggccgtcg acccgttcgc gtgtcccatg atgaccatgc agcgcaagcc cgaggtgcac      60
```

```
gacgccttcc gggaggcggg cccggtcgtc gaggtgaacg cccccgcggg cggacccgcc      120
tgggtcatca ccgatgacgc cctcgcccgc gaggtgctgg ccgatccccg gttcgtgaag      180
gaccccgacc tcgccccgc cgcctggcgg ggggtggacg acggtctcga catccccgtt      240
ccggagctgc gtccgttcac gctcatcgcc gtggacggcg aggcccaccg cgcctgcgc      300 cgcatccacg cacctgcgtt caacccgcgc cggctggccg agcggacgga tcgcatcgcc      360
gcgatcgccg gccggctgct caccgaactc gccgacactt ccggccggtc gggcaaaccg      420
gccgagctga tcggcggctt cgcgtaccac ttcccgctgt tggtcatctg cgagctgctc      480
ggtgtgccgg tcaccgatcc ggcgatggcc cgcgaggccg tcagcgttct caaggcactc      540
ggcctcggcg gcccgcagag cggcggggt gacggcacgg accctgccgg gggcgtgccg      600
gacacctcgg ccctggagag cctgctcctc gaagccgtgc actcagcccg gcggaacgac      660
accccgacca tgacccgcgt gctgtacgag gcgcgcagg ccgagttcgg ctcggtctcc      720
gacgaccagc tcgtctacat gatcaccggg ctcatcttcg ccggccacga caccaccggc      780
tccttcctgg gcttcctgct cgcggaggtc ctggcgggcc gctcgcggc ggatgccgac      840 gaggacgccg tctcccggtt cgtggaggag gcgctgcgct accacccgcc ggtgccctac      900
acgttgtgga ggtcgctgc cacggaggtg accatcggcg gcgtccggct gccccgcgga      960
gcgccggtgc tggtggacat cgagggcacc aacaccgacg ccgccatca cgacgacccg     1020 cacgccttcc acccggaccg tccctcgtgg cggcggctca ccttcggcga cgggccgcac     1080
tactgcatcg gggagcagct cgcccagctg gagtcgcgca cgatgatcgg cgtactgcgc     1140
agcaggttcc ccgaggcccg actggccgtg ccgtacgacg agttgcggtg gtcccggaag     1200
ggggcccaga cggcgcggct caccgaactg cccgtctggc tgcgctga                 1248
```

<210> SEQ ID NO 16
<211> LENGTH: 415
<212> TYPE: PRT
<213> ORGANISM: Artificial sequence
<220> FEATURE:
<223> OTHER INFORMATION: DoxA mutant protein

<400> SEQUENCE: 16

```
Val Ala Val Asp Pro Phe Ala Cys Pro Met Met Thr Met Gln Arg Lys
1               5                   10                  15

Pro Glu Val His Asp Ala Phe Arg Glu Ala Gly Pro Val Val Glu Val
                20                  25                  30

Asn Ala Pro Ala Gly Gly Pro Ala Trp Val Ile Thr Asp Asp Ala Leu
            35                  40                  45

Ala Arg Glu Val Leu Ala Asp Pro Arg Phe Val Lys Asp Pro Asp Leu
        50                  55                  60

Ala Pro Ala Ala Trp Arg Gly Val Asp Asp Gly Leu Asp Ile Pro Val
65                  70                  75                  80

Pro Glu Leu Arg Pro Phe Thr Leu Ile Ala Val Asp Gly Glu Ala His
                85                  90                  95

Arg Arg Leu Arg Arg Ile His Ala Pro Ala Phe Asn Pro Arg Arg Leu
                100                 105                 110

Ala Glu Arg Thr Asp Arg Ile Ala Ala Ile Ala Gly Arg Leu Leu Thr
            115                 120                 125

Glu Leu Ala Asp Thr Ser Gly Arg Ser Gly Lys Pro Ala Glu Leu Ile
        130                 135                 140

Gly Gly Phe Ala Tyr His Phe Pro Leu Leu Val Ile Cys Glu Leu Leu
145                 150                 155                 160
```

Gly Val Pro Val Thr Asp Pro Ala Met Ala Arg Glu Ala Val Ser Val
             165                 170                 175

Leu Lys Ala Leu Gly Leu Gly Gly Pro Gln Ser Gly Gly Gly Asp Gly
         180                 185                 190

Thr Asp Pro Ala Gly Gly Val Pro Asp Thr Ser Ala Leu Glu Ser Leu
     195                 200                 205

Leu Leu Glu Ala Val His Ser Ala Arg Arg Asn Asp Thr Pro Thr Met
 210                 215                 220

Thr Arg Val Leu Tyr Glu Arg Ala Gln Ala Glu Phe Gly Ser Val Ser
225                 230                 235                 240

Asp Asp Gln Leu Val Tyr Met Ile Thr Gly Leu Ile Phe Ala Gly His
             245                 250                 255

Asp Thr Thr Gly Ser Phe Leu Gly Phe Leu Leu Ala Glu Val Leu Ala
         260                 265                 270

Gly Arg Leu Ala Ala Asp Ala Asp Glu Asp Ala Val Ser Arg Phe Val
     275                 280                 285

Glu Glu Ala Leu Arg Tyr His Pro Pro Val Pro Tyr Thr Leu Trp Arg
 290                 295                 300

Phe Ala Ala Thr Glu Val Thr Ile Gly Gly Val Arg Leu Pro Arg Gly
305                 310                 315                 320

Ala Pro Val Leu Val Asp Ile Glu Gly Thr Asn Thr Asp Gly Arg His
             325                 330                 335

His Asp Asp Pro His Ala Phe His Pro Asp Arg Pro Ser Trp Arg Arg
         340                 345                 350

Leu Thr Phe Gly Asp Gly Pro His Tyr Cys Ile Gly Glu Gln Leu Ala
     355                 360                 365

Gln Leu Glu Ser Arg Thr Met Ile Gly Val Leu Arg Ser Arg Phe Pro
 370                 375                 380

Glu Ala Arg Leu Ala Val Pro Tyr Asp Glu Leu Arg Trp Ser Arg Lys
385                 390                 395                 400

Gly Ala Gln Thr Ala Arg Leu Thr Glu Leu Pro Val Trp Leu Arg
             405                 410                 415

<210> SEQ ID NO 17
<211> LENGTH: 1248
<212> TYPE: DNA
<213> ORGANISM: Artificial sequence
<220> FEATURE:
<223> OTHER INFORMATION: doxA gene of Streptomyces

<400> SEQUENCE: 17
gtggccgtcg acccgttcgc gtgtcccatg atgaccatgc agcgcaagcc cgaggtgcac      60
gacgccttcc gggaggcggg cccggtcgtc gaggtgaacg ccccgcgggg cggaccgcc     120 tgggtcatca ccgatgacgc cctcgcccgc gaggtgctgg ccgatccccg gttcgtgaag     180
gaccccgacc tcgccccgc cgcctggcgg ggggtggacg acggtctcga catccccgtt     240
ccggagctgc gtccgttcac gctcatcgcc gtggacggcg aggcccaccg gcgcctgcgc     300
cgcatccacg cacctgcgtt caacccgcgc cggctggccg agcggacgga tcgcatcgcc     360
gcgatcgccg ccggctgct caccgaactc gccgacgcct ccggccggtc gggcaaaccg     420
gccgagctga tcggcggctt cgcgtaccac ttcccgctgt tggtcatctg cgagctgctc     480
ggtgtgccgg tcaccgatcc ggcgatggcc cgcgaggcct cagcgttcct caaggcactc     540
ggcctcggcg gcccgcagag cggcgggggt gacggcacgg accctgccgg gggcgtgccg     600

-continued

```
gacacctcgg ccctggagag cctgctcctc gaagccgtgc actcagcccg gcggaacgac    660
accccgacca tgaccgcgt gctgtacgag cgcgcgcagg ccgagttcgg ctcggtctcc    720
gacgaccagc tcgtctacat gatcaccggg ctcatcttcg ccggccacga caccaccggc    780
tccttcctgg gcttcctgct cgcggaggtc ctggcgggcc gctcgcggc ggatgccgac    840 gaggacgccg tctcccggtt cgtggaggag gcgctgcgct accacccgcc ggtgccctac    900
acgttgtgga ggtcgctgc cacggaggtg accatcggcg cgtccggct gccccgcgga    960 gcgccggtgc tggtggacat cgagggcacc aacaccgacg ccgccatca cgacgccccg   1020 cacgccttcc accggaccg tccctcgtgg cggcggctca ccttcggcga cgggccgcac   1080
tactgcatcg gggagcagct cgcccagctg gagtcgcgca cgatgatcgg cgtactgcgc   1140
agcaggttcc ccgaggcccg actggccgtg ccgtacgacg agttgcggtg gtgccggaag   1200
ggggcccaga cggcgcggct caccgaactg cccgtctggc tgcgctga                 1248
```

<210> SEQ ID NO 18
<211> LENGTH: 415
<212> TYPE: PRT
<213> ORGANISM: Artificial sequence
<220> FEATURE:
<223> OTHER INFORMATION: Dox A protein of Streptomyces

<400> SEQUENCE: 18

```
Val Ala Val Asp Pro Phe Ala Cys Pro Met Met Thr Met Gln Arg Lys
1               5                   10                  15

Pro Glu Val His Asp Ala Phe Arg Glu Ala Gly Pro Val Val Glu Val
            20                  25                  30

Asn Ala Pro Ala Gly Gly Pro Ala Trp Val Ile Thr Asp Asp Ala Leu
        35                  40                  45

Ala Arg Glu Val Leu Ala Asp Pro Arg Phe Val Lys Asp Pro Asp Leu
    50                  55                  60

Ala Pro Ala Ala Trp Arg Gly Val Asp Gly Leu Asp Ile Pro Val
65                  70                  75                  80

Pro Glu Leu Arg Pro Phe Thr Leu Ile Ala Val Asp Gly Glu Ala His
                85                  90                  95

Arg Arg Leu Arg Arg Ile His Ala Pro Ala Phe Asn Pro Arg Arg Leu
            100                 105                 110

Ala Glu Arg Thr Asp Arg Ile Ala Ala Ile Ala Gly Arg Leu Leu Thr
        115                 120                 125

Glu Leu Ala Asp Ala Ser Gly Arg Ser Gly Lys Pro Ala Glu Leu Ile
    130                 135                 140

Gly Gly Phe Ala Tyr His Phe Pro Leu Leu Val Ile Cys Glu Leu Leu
145                 150                 155                 160

Gly Val Pro Val Thr Asp Pro Ala Met Ala Arg Glu Ala Val Ser Val
                165                 170                 175

Leu Lys Ala Leu Gly Leu Gly Gly Pro Gln Ser Gly Gly Gly Asp Gly
            180                 185                 190

Thr Asp Pro Ala Gly Gly Val Pro Asp Thr Ser Ala Leu Glu Ser Leu
        195                 200                 205

Leu Leu Glu Ala Val His Ser Ala Arg Arg Asn Asp Thr Pro Thr Met
    210                 215                 220

Thr Arg Val Leu Tyr Glu Arg Ala Gln Ala Glu Phe Gly Ser Val Ser
225                 230                 235                 240

Asp Asp Gln Leu Val Tyr Met Ile Thr Gly Leu Ile Phe Ala Gly His
                245                 250                 255
```

-continued

```
Asp Thr Thr Gly Ser Phe Leu Gly Phe Leu Leu Ala Glu Val Leu Ala
            260             265             270

Gly Arg Leu Ala Ala Asp Ala Asp Glu Asp Ala Val Ser Arg Phe Val
            275             280             285

Glu Glu Ala Leu Arg Tyr His Pro Pro Val Pro Tyr Thr Leu Trp Arg
    290             295             300

Phe Ala Ala Thr Glu Val Thr Ile Gly Gly Val Arg Leu Pro Arg Gly
305             310             315             320

Ala Pro Val Leu Val Asp Ile Glu Gly Thr Asn Thr Asp Gly Arg His
            325             330             335

His Asp Ala Pro His Ala Phe His Pro Asp Arg Pro Ser Trp Arg Arg
            340             345             350

Leu Thr Phe Gly Asp Gly Pro His Tyr Cys Ile Gly Glu Gln Leu Ala
            355             360             365

Gln Leu Glu Ser Arg Thr Met Ile Gly Val Leu Arg Ser Arg Phe Pro
    370             375             380

Glu Ala Arg Leu Ala Val Pro Tyr Asp Glu Leu Arg Trp Cys Arg Lys
385             390             395             400

Gly Ala Gln Thr Ala Arg Leu Thr Glu Leu Pro Val Trp Leu Arg
            405             410             415
```